United States Patent
Jayasuriya et al.

(10) Patent No.: US 11,241,504 B2
(45) Date of Patent: Feb. 8, 2022

(54) THERMORESPONSIVE INJECTABLE MICROPARTICLES-GEL COMPOSITES WITH LOW DOSE OF RECOMBINANT BMP-9 AND VEGF FOR BONE REPAIR

(71) Applicant: The University of Toledo, Toledo, OH (US)

(72) Inventors: Ambalangodage C. Jayasuriya, Toledo, OH (US); Bipin Gaihre, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 16/934,474

(22) Filed: Jul. 21, 2020

(65) Prior Publication Data

US 2021/0023240 A1    Jan. 28, 2021

Related U.S. Application Data

(60) Provisional application No. 62/877,063, filed on Jul. 22, 2019.

(51) Int. Cl.

| | | |
|---|---|---|
| *A61K 38/18* | (2006.01) | |
| *A61K 47/32* | (2006.01) | |
| *A61K 47/34* | (2017.01) | |
| *A61K 47/69* | (2017.01) | |

(52) U.S. Cl.
CPC ...... *A61K 47/6903* (2017.08); *A61K 38/1875* (2013.01); *A61K 47/32* (2013.01); *A61K 47/34* (2013.01)

(58) Field of Classification Search
CPC ..... A61K 38/1875; A61K 47/32; A61K 47/34
See application file for complete search history.

(56) References Cited

U.S. PATENT DOCUMENTS 6,287,588 B1 *  9/2001  Shih
6,369,039 B1 *  4/2002  Palasis
6,497,902 B1 * 12/2002  Ma

OTHER PUBLICATIONS

Altomare et al. (J Mater Sci: Mater Med, published 2016, pp. 1-13) (Year: 2016).*
Mitra et al. (Indian J Pharm Sci. published 2011, pp. 355-366) (Year: 2011).*

* cited by examiner

*Primary Examiner* — Alma Pipic
(74) *Attorney, Agent, or Firm* — MacMillan, Sobanski & Todd, LLC

(57) ABSTRACT

Compositions for delivering one or more active substances, or for repairing a bone, and methods of making and using the same, are described.

15 Claims, 21 Drawing Sheets
(20 of 21 Drawing Sheet(s) Filed in Color)

THERMORESPONSIVE INJECTABLE MICROPARTICLES-GEL COMPOSITES WITH LOW DOSE OF RECOMBINANT BMP-9 AND VEGF FOR BONE REPAIR

RELATED APPLICATIONS

This application claims priority to U.S. Provisional Application Ser. No. 62/877,063 filed under 35 U.S.C. § 111(b) on Jul. 22, 2019, the disclosure of which is incorporated herein by reference in its entirety.

STATEMENT REGARDING FEDERALLY SPONSORED RESEARCH

This invention was made with government support under grant number DE023356 awarded by the National Institutes of Health. The government has certain rights in this invention.

BACKGROUND

The inherent limitations of currently available bone repair techniques using autograft and allograft have prompted a demand for new scaffolds that can effectively combine key components of bone tissue engineering, such as osteogenic progenitor cells, osteoinductive factors, and osteoconductive materials. In particular, there is a need for injectable scaffolds that can undergo a sol-gel transition at physiological conditions. It would be advantageous to develop new and improved compositions and methods for this purpose.

SUMMARY

Provided is a composition comprising polymer microparticles coated with a first active substance; and a thermoresponsive hydrogel comprising a polymer and a crosslinker.

In certain embodiments, the thermoresponsive hydrogel comprises methylcellulose, alginate, or a combination thereof. In certain embodiments, the crosslinker comprises calcium. In certain embodiments, the polymer microparticles comprise chitosan, cellulose, polystyrene, polyethylene, poly lactic acid (PLA), poly(lactic-co-glycolic acid) (PLGA), or a combination thereof. In certain embodiments, the polymer microparticles comprise chitosan crosslinked with tripolyphosphate (TPP).

In certain embodiments, the first active substances comprises a drug, polymer, protein, peptide, oligonucleotide, cells such as stem cells, dye, antigen, antibody, or combination thereof. In certain embodiments, the first active substance is present at a dose of from about 500 ng/ml to about 1 µg/ml. In certain embodiments, the first active substance comprises a bone morphogenic protein (BMP). In certain embodiments, the first active substance comprises BMP-2, BMP-7, BMP-9, or a combination thereof.

In certain embodiments, the thermoresponsive hydrogel comprises a second active substance. In particular embodiments, the second active substance comprises a drug, polymer, protein, peptide, oligonucleotide, cells such as stem cells, dye, antigen, antibody, or combination thereof. In particular embodiments, the second active substance is the same as the first active substance. In particular embodiments, the second active substance is different from the first active substance. In particular embodiments, the second active substance is present at a dose of from about 500 ng/ml to about 1 µg/ml. In particular embodiments, the second active substance comprises a small molecule or a protein. In particular embodiments, the second active substance comprises vascular endothelial growth factor (VEGF). In particular embodiments, the first active substance comprises a bone morphogenic protein (BMP), and the second active substance comprises VEGF. In particular embodiments, the first active substance consists essentially of a bone morphogenic protein (BMP), and the second active substance consists essentially of VEGF.

In certain embodiments, the first active substance is capable of controlled release over a period of several weeks in vivo. In certain embodiments, the second active substance is capable of controlled release over a period of several weeks in vivo. In certain embodiments, each of the first active substance and the second active substance is capable of controlled release over a period of several weeks in vivo.

In certain embodiments, the polymer microparticles have a size ranging from about 300 µm to about 1 mm. In certain embodiments, the polymer microparticles have a size ranging from about 500 µm to about 800 µm.

In certain embodiments, the composition gels at body temperature. In certain embodiments, the composition is a semi-solid at room temperature. In certain embodiments, the composition is a liquid at 0° C.

In certain embodiments, the polymer is present in the thermoresponsive hydrogel at a concentration ranging from about 2% by weight to about 10% by weight. In certain embodiments, the polymer is present in the thermoresponsive hydrogel at a concentration ranging from about 3% by weight to about 7% by weight.

Further provided is a composition comprising chitosan microparticles coated with BMP-2, BMP-7, BMP-9, or a combination thereof. In certain embodiments, the chitosan microparticles are crosslinked with tripolyphosphate (TPP). In certain embodiments, the chitosan microparticles have an average size ranging from about 300 µm to about 1 mm. In certain embodiments, the chitosan microparticles have an average size ranging from about 500 µm to about 800 µm.

Further provided is a composition comprising a thermoresponsive hydrogel comprising methylcellulose, wherein the hydrogel is capable of degrading within 12 weeks in vivo. In certain embodiments, the composition further comprises alginate. In certain embodiments, the composition further comprises a crosslinker. In particular embodiments, the crosslinker comprises calcium.

Further provided is a composition comprising a thermoresponsive hydrogel formed from methylcellulose, wherein the thermoresponsive hydrogel further comprises VEGF. In certain embodiments, the composition further comprises alginate. In certain embodiments, the composition further comprises a crosslinker. In particular embodiments, the crosslinker comprises calcium.

Further provided is a method for making a bone repair composition, the method comprising coating polymer microparticles with a first active substance to form coated microparticles; and adding the coated microparticles to a thermoresponsive hydrogel to make a bone repair composition. In certain embodiments, the bone repair composition is capable of gelling at physiologic temperature. In certain embodiments, the composition is a semi-solid at room temperature. In certain embodiments, the polymer microparticles have an average size ranging from about 300 µm to about 1 mm. In certain embodiments, the polymer microparticles have an average size ranging from about 500 µm to about 800 µm. In certain embodiments, the polymer microparticles are prepared by crosslinking chitosan with tripolyphosphate (TPP). In particular embodiments, the polymer microparticles are rinsed and dried to obtain microparticles having a size ranging from about 500 μm to about 800 μm.

Further provided is a method for repairing a bone, the method comprising administering a composition to a bone, wherein the composition is at a temperature of less than room temperature when administered, the composition comprising polymer microparticles coated with a first active substance in a thermoresponsive hydrogel. In certain embodiments, the temperature is about 0° C. when administered. In certain embodiments, the thermoresponsive hydrogel comprises methylcellulose, alginate, and a crosslinker. In certain embodiments, the polymer microparticles comprise chitosan crosslinked with tripolyphosphate (TPP). In certain embodiments, the thermoresponsive hydrogel comprises methylcellulose, alginate, and a crosslinker.

Further provided is a kit comprising a first container housing polymer microparticles coated with a first active substance; and a second container housing a thermoresponsive hydrogel. In certain embodiments, the thermoresponsive hydrogel comprises a second active substance. In certain embodiments, the first container and/or the second container is kept at a temperature below room temperature.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIG. 3D shows the cumulative release profile of BMP-3 from MPs only, and FIG. 3E shows the cumulative release profile of BMP-9 and VEGF from MPs-gel scaffold.

FIGS. 4B-4C show osteogenic differentiation of hMSCs in 2-D culture with and without 100 ng/ml BMP-9 and in the presence of normal media and osteogenic media determined using ALP expression (FIG. 4B) and Alizarin red staining in the presence of osteogenic media (FIG. 4C).

FIGS. 5A-5B show attachment and proliferation of hMSCs (FIG. 5A) and rMSCs (FIG. 5B) on BMP-9 coated and non-coated MPs. FIGS. 5C-5D show viability of hMSCs encapsulated within MPs-gel (FIG. 5C) and their mineral deposition shown by Von-kossa staining (i-without cells; ii-MPs-gel; iii-MPs-gel+V; iv-MPs-gel+V+B) (FIG. 5D). FIGS. 5E-5H show osteogenic differentiation of hMSCs within MPs-gel determined using ALP quantification (FIG. 5E), and osteogenic gene expressions (FIGS. 5F-5H). The dotted red line shows the reference level of MPs-gel as a control.

FIG. 7A shows 3-D reconstructed images of defect site after week 6 and week 12. New bone formation on the defect region was more prominent in the MPs-gel+V+B group with higher bone growing in the defect region, whereas the defect site was still not healing on void and MPs-gel groups. At 12 weeks, the defects injected with MPs-gel+V+B was completely healed with all the empty region filled with new bone. FIG. 7B shows quantification of bone volume along the defect site with the diameter of 3.5 mm at week 12, and FIG. 7C shows quantification of bone volume along the defect site at week 6. These charts show there was no significant difference in bone volume between the groups after 6 weeks. However, at 12 weeks, the bone volume was significantly higher in the MPs-gel+V+B group compared to void ($p<0.05$) and MPs-gel ($p<0.001$) groups.

FIGS. 8A, 8B show void defect. FIGS. 8C, 8D show MPs-gel. FIGS. 8E, 8F show MPs-gel+V+B. The dotted black rectangles in FIGS. 8A, 8C, and 8E show the area magnified at 20× shown in FIGS. 8B, 8D, and 8F, respectively. FT: Fibrous connective tissue, HB: Host bone, NB: New bone. Black arrows: osteoblasts. Green arrows: osteocytes. Blue arrows: osteoid. Red arrows: blood vessels.

DETAILED DESCRIPTION

Figure 1:
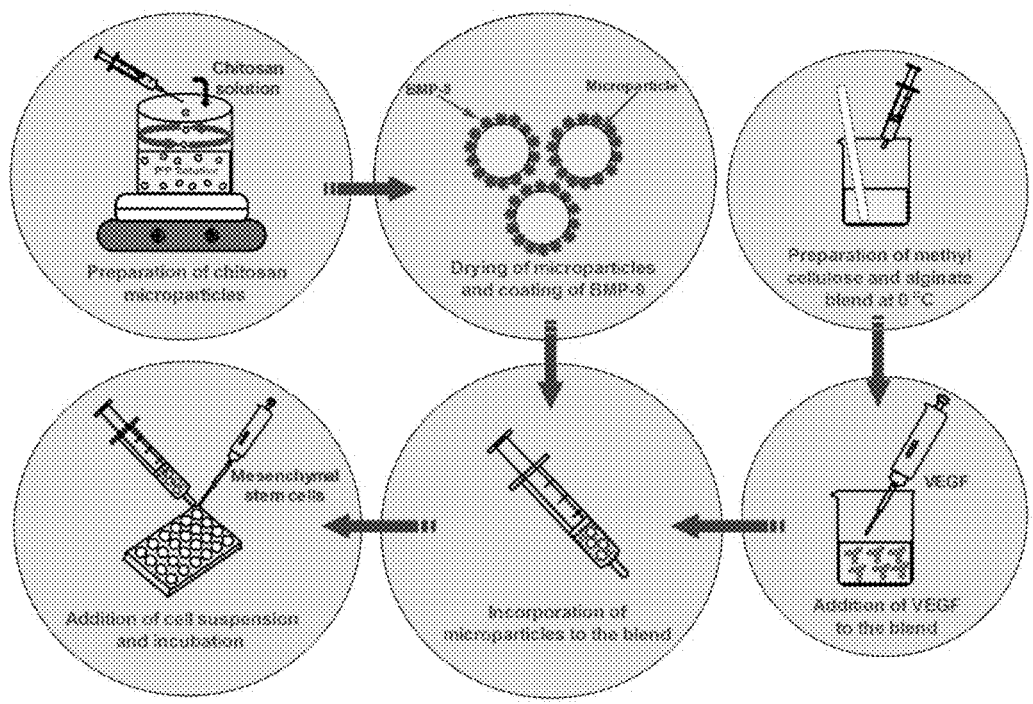
FIG. 1: Scheme 1, showing a schematic representation of the preparation and in vitro analysis of a microparticles (MPs)-gel system described in the examples herein.

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

In situ gelling scaffolds offer a good mobility at room temperature, making them easy to be injected in liquid form. This leads to additional benefits of the scaffold such as a good adaptation to the defect margins, good bioadhesion, and a suitable niche for growth factors and cells. Provided herein is a composition that may act as an in situ gelling scaffold for delivering one or more active substances, and the components making up the composition, which may each individually be useful to deliver an active substance, in a controlled manner.

While injectable hydrogels have shown potential in therapeutic delivery over the past few decades, a complex multicomponent system capable of releasing multiple therapeutics in a temporally controlled manner is still unrealized. In accordance with the present disclosure, such a system can be formed by pre-loading a first active substance into polymeric microparticles (MPs) and integrating the MPs into a hydrogel containing a second active substance. In tissue regeneration studies, MPs with the injectable size ranging from 10 μm to 1000 μm are being used as solid scaffolds mostly through sintering or chemical agglomeration. These processes, however, take away the injectability property of these MPs. The MPs incorporated into the hydrogel-containing compositions herein, however, can be a better scaffold option as both the injectability and scaffold-like property of the MPs can be preserved.

In general, a composition may include a microparticle component and a gel component. The microparticle component may be encapsulated within the gel. The microparticle component is composed of polymer microparticles that may be coated with a first active substance. The gel component is composed of a thermoresponsive hydrogel. The thermoresponsive hydrogel may include a second active substance. The microparticle component can be mixed with the gel component to encapsulate the microparticles in the hydrogel. The mixing may be conducted a temperature below the temperature at which the thermoresponsive hydrogel solidifies, or even below the temperature at which the thermoresponsive hydrogel becomes a semi-solid. Upon mixing, the composition may be stored at such low temperatures so as to prevent solidification. When desired, the composition may be injected and, upon reaching an elevated temperature such as body temperature (i.e., 37° C.), the thermoresponsive hydrogel will undergo a sol-gel reaction and solidify into a solid. Once placed in or around a desired anatomical location, the composition will degrade over time, releasing the first active substance and, if present, the second active substance over time. The controlled release of the first active substance and, if present, the second active substance may be tailored or customized for the desired application, for example by adjusting the molecular weight of the polymer(s) used to form the polymer microparticles and the thermoresponsive hydrogel, or the amount of crosslinking of such polymers.

The polymer microparticles may be formed from any suitable polymer capable of forming microparticles. Non-limiting example polymers for forming the polymer microparticles include chitosan, cellulose, polystyrene, polyethylene, poly lactic acid (PLA), poly(lactic-co-glycolic acid) (PLGA), and combinations thereof. The polymer microparticles may be formed from a natural polymer, a synthetic polymer, or a combination thereof. In one non-limiting example, chitosan (CS), a naturally derived biocompatible polymer, may be used to prepare the microparticles through facile fabrication techniques in benign conditions. These microparticles have been used in a wide array of drug delivery and tissue regeneration applications. Tissue specific regeneration has been achieved with these microparticles through various biological and chemical surface treatments.

A chitosan solution can be added to a crosslinker solution of tripolyphosphate (TPP), and chitosan microparticles may be obtained. The polymer microparticles may have a size ranging from about 300 μm to about 1 mm. In some embodiments, the polymer microparticles may have a size ranging from about 500 μm to about 800 μm. The size of the polymer microparticles impacts the viscosity and injectability of the resulting composition. Thus, the size of the polymer microparticles may be adjusted or tailored based on the desired viscosity and injectability of the final composition. For example, if the composition is intended to be injected through a 13 G or a 16 G needle, then the polymer microparticles should have a size ranging from about 500 μm to about 800 μm. The size of the polymer microparticles may be controlled, for example, by conducting an additional rinsing and drying step after forming the polymer microparticles. For example, the polymer microparticles may be prepared by combining chitosan with TPP and stirring for a period of time, then drying. Then, the microparticles may be further rinsed with deionized (DI) water under stirring conditions for a period of time, such as an hour, and dried again so as to produce a slightly reduced size of microparticles. Advantageously, when this additional rinsing and drying step is conducted with chitosan-TPP microparticles, the microparticles can have a size making them suitable for injection applications using a 13 G or 16 G needle. Furthermore, the additional rising and drying step avoids having to use organic solvents to obtain smaller microparticles, thereby avoiding possible toxicity concerns.

Once formed, the polymer microparticles may be washed and/or dried prior to coating them with the first active substance. The first active substance may then be coated onto the polymer microparticles. Advantageously, the first active substance may be coated onto the polymer microparticles instead of being encapsulating within the polymer microparticles, which provides for more desirable release properties. The first active substance may be any drug, polymer, protein, peptide, oligonucleotide, cells such as stem cells, dye, antigen, antibody, or any combination thereof. In some embodiments, the first active substance is a bone morphogenic protein (BMP), such as BMP-2, BMP-4, BMP-6, BMP-7, or BMP-9. In some embodiments, the first active substance is a combination of any two or each of BMP-2, BMP-7, and BMP-9. In one non-limiting example, the first active substance is BMP-9. In other embodiments, the first active substance is a drug, such as an antibiotic. In one non-limiting example, the first active substance is vancomycin.

BMPs are potent osteoinductive factors. BMP-2/4/6/7/9 have been known as osteogenic BMPs, as they have the ability to induce the osteoblasts differentiation and bone formation. Several comprehensive studies have shown BMP-9 to be the most osteogenic and have shown that the SMAD phosphorylation induced by BMP-9, a major pathway in osteogenic differentiation, was not prevented by noggin, which is a well-known antagonist of the BMP pathway. Most of the studies showing the osteogenic application of BMP-9 in bone regeneration, however, involve the BMP-9 expressing adenoviral transfection of osteoprogenitor or stem cells. While the results with gene therapy are efficient, the viral nature and lack of control makes this technique problematic in bone regeneration.

The thermoresponsive hydrogel may be formed from any polymer or combination of polymers which is capable of swelling with water and gelling at a desired temperature, and may optionally include a crosslinker A crosslinker may prevent the burst release of a second active substance included in the thermoresponsive hydrogel. Non-limiting examples of suitable polymers include methylcellulose, alginate, chitosan, polyethylene glycol (PEG), collagen, gelatin, starch, agarose, or combinations thereof. The polymer(s) may be present in the thermoresponsive hydrogel at a concentration ranging from about 2% to about 10% by weight, or from about 3% to about 7% by weight. However, other concentrations are possible, though the resulting thermoresponsive hydrogel may not have a desirable viscosity for injectability at other concentrations of polymer.

The thermoresponsive hydrogel may be formed from natural or synthetic polymers, or blends thereof. In some embodiments, the thermoresponsive hydrogel is formed from only biocompatible polymers such as methylcellulose and alginate. Methylcellulose (MC) and alginate (Alg) are naturally derived biocompatible polymers readily soluble in water. MC has been widely used as a binder or viscosity-enhancing polymer in food, pharmaceutical, and ceramic industries. When a MC solution is heated to a sufficient temperature, MC precipitates out of solution and forms a gel. The use of MC only as a hydrogel for tissue regeneration applications is mostly limited by its gelation temperature, which is higher than the physiological temperature. Furthermore, gel strength in cell culture and in vivo conditions is problematic, as a slight variation in temperature can affect its stability. One of the ways to modify or enhance the physical properties of MC is by blending it with another polymer.

Alg has been studied in tissue engineering and drug delivery applications. Alg forms a crosslinked complex with polyvalent cations. Alg complexes with calcium are used in the form of microgels, microcapsules, scaffolds, and hydrogels in biomedical applications. MC blended with Alg has been previously explored to develop a pH sensitive controlled release systems. MC is also used to improve the extrusion based 3-D printing of alginate owing to the high viscosity of MC.

In one non-limiting example, the thermoresponsive hydrogel is formed from a blend of MC and Alg with calcium (e.g., in the form of $CaCl_2$) or any other salt) as a crosslinker. As shown in the examples herein, this thermoresponsive hydrogel is capable of gelling at physiologic temperature, and controllably releasing the coated polymer microparticles in vivo.

The thermoresponsive hydrogel may further include a second active substance, which can simply be added to the thermoresponsive hydrogel when in solution. The second active substance may be any drug, polymer, protein, peptide, oligonucleotide, cells such as stem cells, dye, antigen, antibody, or any combination thereof. The second active substance may be the same, or may be different from, the first active substance. In one non-limiting example, the second active substance is vascular endothelial growth factor (VEGF). As shown in the examples herein, the combination of BMP-9 and VEGF delivered by the composition advantageously forms new bone with new blood vessels after 12 weeks. Thus, in one non-limiting example composition, the first active substance is BMP-9 and the second active substance is VEGF. In other embodiments, the composition does not include a second active substance.

Numerous combinations of first and second active substances are possible and entirely encompassed within the scope of the present disclosure. In some embodiments, the first active substance comprises a bone morphogenic protein (BMP), and the second active substance comprises VEGF. In some embodiments, the first active substance comprises a BMP and the second active substance comprises an antibiotic. In some embodiments, the first active substance comprises an antibiotic and the second active substance comprises VEGF. In some embodiments, the first active substance comprises an antibiotic, and the second active substance is not present. In some embodiments, the first active substance comprises a combination of a BMP and an antibiotic, and the second active substance comprises VEGF. In some embodiments, the first active substance comprises a combination of a BMP and an antibiotic, and the second active substance is not present. In some embodiments, the first active substance comprises VEGF, and the second active substance comprises a BMP. In some embodiments, the first active substance comprises a combination of one or more BMPs and VEGF, and the second active substance is not present. In some embodiments, the first active substance comprises a combination of one or more BMPs and VEGF, and the second active substance comprises an antibiotic.

The first active substance may be incorporated into the polymer microparticles at a lower dose than conventionally required for effectiveness. Similarly, the second active substance, if present, may be incorporated into the thermoresponsive hydrogel at a lower dose than conventionally required for effectiveness. For example, each of the first active substance and the second active substance may be in the composition at a concentration ranging from about 500 ng/ml to about 1 μg/ml.

The polymer microparticles and the thermoresponsive gel can be prepared separately, and then either stored separately or combined. If stored separated before being combined, the polymer microparticles and the thermoresponsive gel may be stored at a temperature low enough to preserve the bioactivity of any active substances, for example at about 0° C. Similarly, the combining of these components may be undertaken a temperature low enough to prevent the thermoresponsive hydrogel from gelling or solidifying, and low enough to preserves the bioactivity of any active substances. For example, the polymer microparticles and the thermoresponsive gel may be combined at a temperature of about 0° C. In some examples, the polymer microparticles and the thermoresponsive gel may be combined at room temperature still without gelling of the thermoresponsive hydrogel. Once combined, the resulting solution may be stored at a low enough temperature to prevent the thermoresponsive hydrogel from gelling or solidifying, such as 0° C. or, in some embodiments, room temperature. When desired, the composition may be injected or otherwise inserted to a desired anatomical location. The physiologic temperature may cause the thermoresponsive hydrogel to undergo a sol-gel reaction and harden in place.

As the animal studies described in the examples herein demonstrate, over time the thermoresponsive hydrogel may be absorbed or degraded in vivo. As this happens, the composition releases the coated microparticles, which in turn degrade in vivo thereby releasing the first active substance. Similarly, as the thermoresponsive hydrogel is being absorbed or degraded by the body, the composition releases the second active substance, if present. Thus, the release rates of the first active substance and the second active substance can be adjusted by altering the rate at which the thermoresponsive hydrogel is degraded in vivo, which can be tailored by adjusting the molecular weight of the polymer(s) used to form the polymer microparticles and the thermoresponsive hydrogel. In general, the larger the molecular weight of the polymer(s) used to form the polymer microparticles and thermoresponsive hydrogel, the longer it will take for the first active substance and, if present, the second active substance to be released from the composition. Furthermore, the release rate of the first active substance can be tailored by adjusting the amount of cross-linking of the polymer microparticles (i.e., adjusting the amount of crosslinker added to form the polymer microparticles). In general, the greater the amount of crosslinking of the polymer microparticles, the slower the release rate of the first active substance will be. Additionally, the size of the polymer microparticles may impact how long the polymer microparticles take to degrade in vivo. Thus, for example, two or more types of polymer microparticles having multiple sizes can be combined so as to produce different release rates of the first active substance. Also, in embodiments wherein the polymer microparticles are formed from chitosan, the degree of deactylation of the chitosan may affect the rate at which the polymer microparticles degrade in vivo. In some embodiments, the polymer microparticles may last several months in vivo.

Advantageously, the compositions described herein may be useful for various purposes such as repairing a bone, forming new blood vessels, or for forming cartilage, depending on the identity of the first active substance and, if present, the identity of the second active substance. For example, in embodiments in which the first active substance and/or second active substance includes BMPs and/or VEGF, the composition is useful for repairing a bone. As shown in the examples herein, administering such a composition may result in new bone formation and new blood vessel formation after several weeks.

It is further envisioned that the compositions and methods described herein can be embodied in the form of a kit or kits. A non-limiting example of such a kit is a kit for repairing a bone, the kit comprising polymer microparticles coating with a first active substance, and a thermoresponsive hydrogel, in separate containers, where the containers may or may not be present in a combined configuration. Many other kits are possible, such as a kit further include dry ice, a thermos, or other means for keeping the composition below room temperature. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive or CD-ROM. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

In the present examples, the results of subcutaneous and cranial bone formation induced by BMP-9 delivered using CS MPs incorporated thermoresponsive gel are described. The dose of BMP-9 used in these examples is much less than that which has been reported for BMP-9 to induce the in vivo bone formation. The gel itself was loaded with VEGF to facilitate the neovascularization. VEGF is considered as one of the key regulators of angiogenesis during bone formation and has been shown to disrupt the normal fracture healing when inhibited. The multicomponent releasing MPs-gel system mimics a temporal release profile of BMP-9 and VEGF during the normal bone healing process where VEGF expression is higher compared to that of BMPs. The in situ gelling combination of MC and Alg was able to localize the BMP-9 coated MPs at the subcutaneous injection site of rats and thus can improve the therapeutic efficacy of BMP-9 at a target site.

Figure 9:
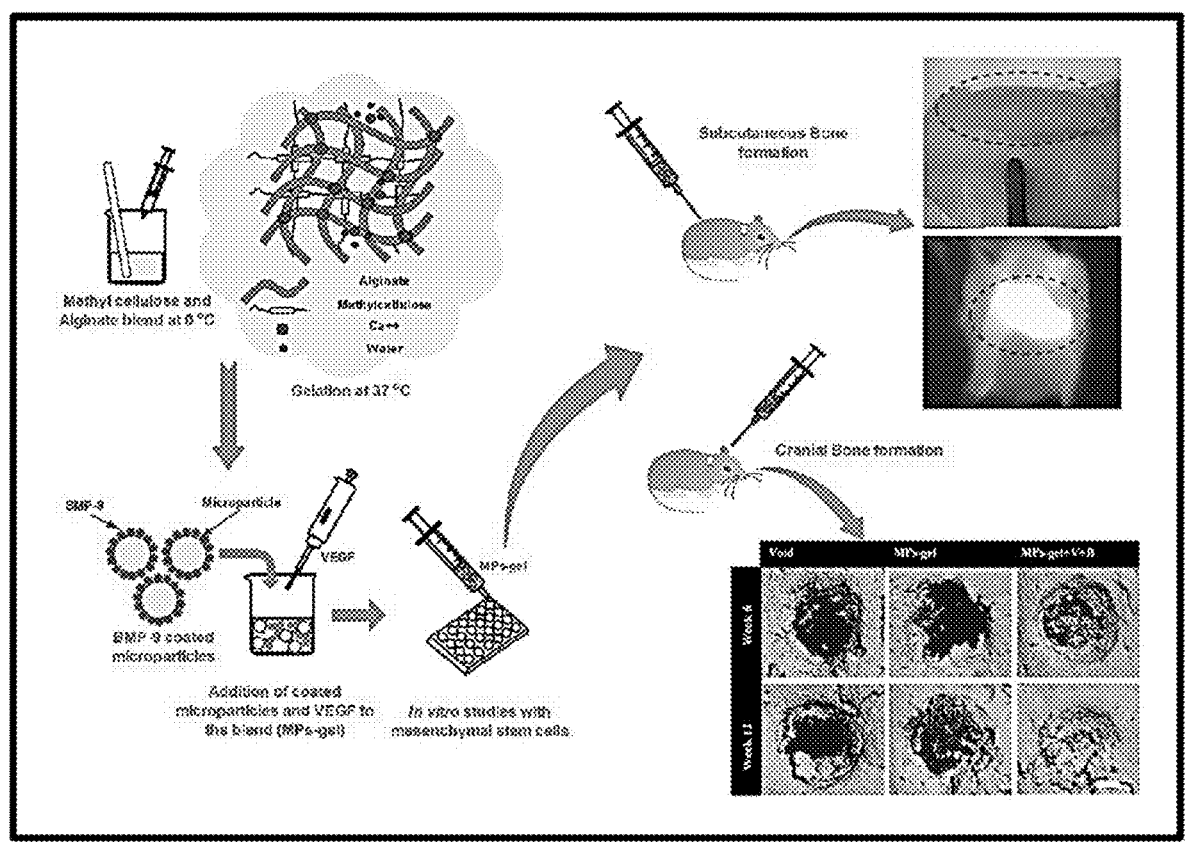
FIG. 9: Illustration depicting various processes and results of the examples described herein.
Figure 10:
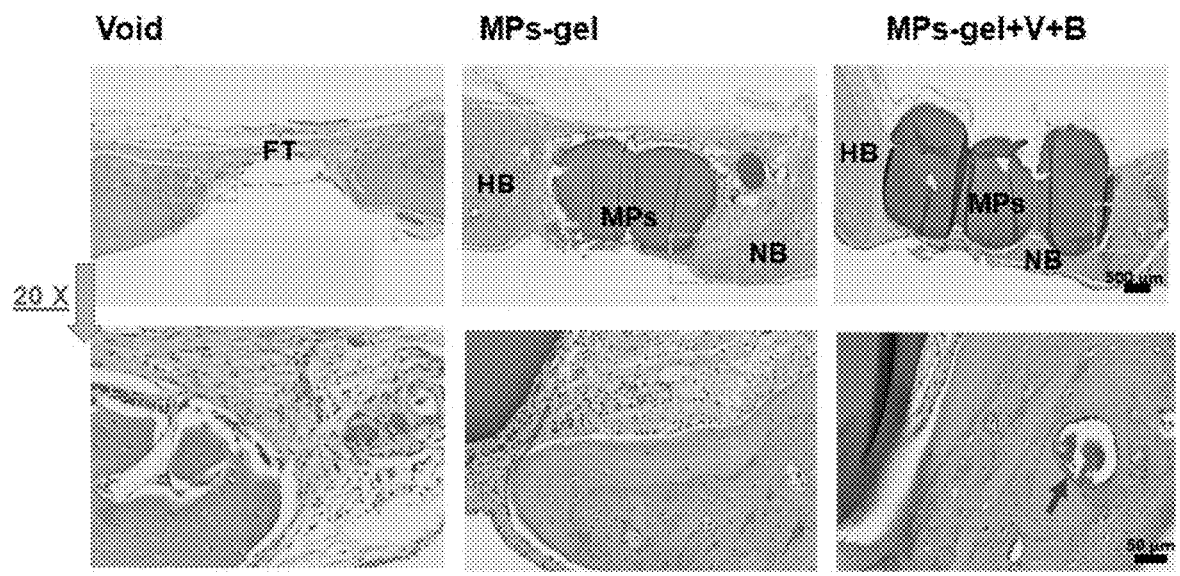
FIG. 10: Hematoxylin and Eosin stained sections of bone tissue harvested from the defect site showing the nature of new bone formation at week 6 and week 12. On the top, the sections from tissues harvested after 6 weeks are shown. The defect site in the void group was mostly occupied by the fibrous tissue which was similar in MPs-gel group where very little bone ingrowth occurred from the host bone into the defect. MPs-gel+V+B group, however, showed the new bone formation on the defect site. Magnified images further showed the presence of blood vessels on these groups along with osteocytes. On the bottom, the sections harvested after 12 weeks are shown. The bone formation in the void group and the MPs-gel group was less and the new bone was immature fibrous bone with the defect still significantly occupied by the fibrous tissues. The new bone formation on MPs-gel+V+B group was more mature and bridged the gap between the defects. Blood vessels and osteocytes were abundantly present. FT: fibrous connective tissue. HB: host bone. NB: new bone. Black arrows: osteoblasts. Green arrows: osteocytes. Red arrows: blood vessels.
Figure 10:
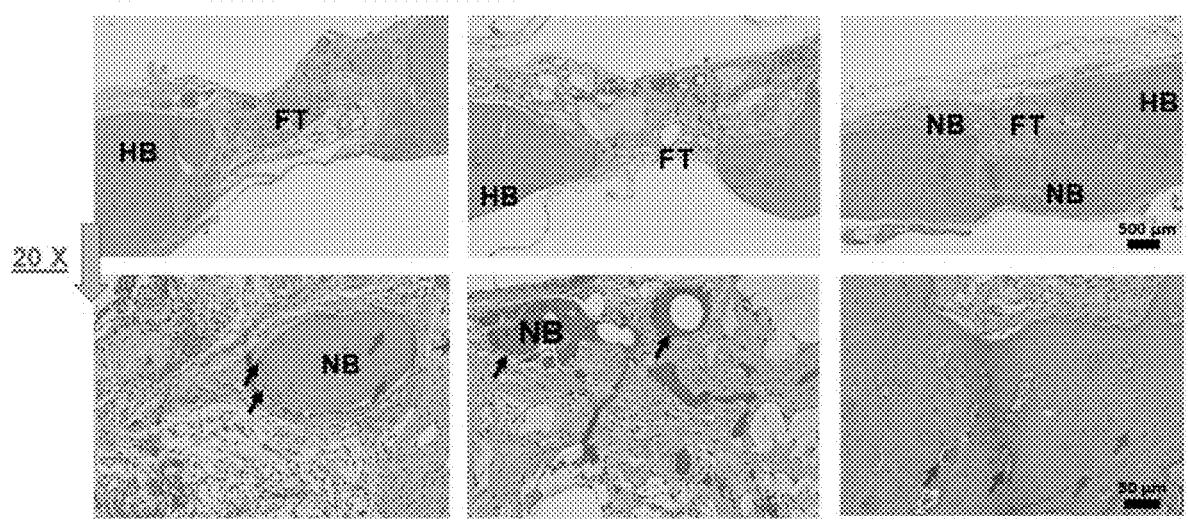

FIG. 9 shows an illustration depicting various processes and results described in these examples.

Materials

Methylcellulose with a viscosity of 15 cP (2% w/v in water at 20° C.), sodium alginate, chitosan (75-85% deacetylation), sodium tripolyphosphate (85%), β-glycerol phosphate (≥98.0%), L-ascorbic acid (cell culture tested), and dexamethasone were all purchased from Sigma-Aldrich (St. Louis, Mo.). Calcium chloride was purchased from Fisher Scientific (Waltham, Mass.). Recombinant BMP-9 and VEGF along with their corresponding ELISA kits were purchased from R&D Systems (Minneapolis, Minn.). Human bone marrow mesenchymal stem cells, xenofree medium (StemPro), Dulbecco's minimum essential medium (DMEM, Gibco), alpha minimum essential medium (α-MEM, Gibco), fetal bovine serum (FBS, Gibco), penicillin-streptomycin (Gibco), gentamicin (Gibco), and live and dead cell assay kit (Invitrogen) were all purchased from ThermoFisher scientific (Waltham, Mass.) Alkaline phosphatase (ALP) assay kit was purchased from BioVision Incorporated (San Francisco, Calif.).

Synthesis of Microparticles

Chitosan (CS) microparticles (MPs) were fabricated using a simple coacervation technique with sodium tripolyphosphate (TPP) as a crosslinker Briefly, 2% (w/v) CS solution was added dropwise to 2% (w/v) TPP solution using a syringe and 30 G needle under stirring condition for 1 h 30 min at 300 rpm. The thus obtained CS beads were then separated from the TPP solution, washed with deionized (DI) water, and dried inside the fume hood to get the MPs. The dried MPs were further rinsed with DI water under stirring condition for 1 h and dried again inside the fume hood. This process allowed for the production of slightly reduced size MPs that made them suitable for injection applications using 13 or 16 G needles.

Synthesis of Gel

All of the polymer solutions used in the synthesis of gel were prepared under the sterile condition. 10% (w/v) methyl cellulose (MC) solution was prepared by dispersing the MC on a beaker containing hot DI water under stirring condition (1000 rpm, 85° C.) for 15 min. The temperature was then reduced to 55° C., and 0.3% (w/v) calcium chloride ($CaCl_2$) was added to the dispersion and the stirring was continued for 15 min. The dispersion was then cooled down by transferring the beaker to the ice bath and letting the MC solubilize. As the temperature was lowered, a clear MC solution was obtained. The solution was allowed to equilibrate by storing it overnight at 4° C. The solution was stored at the same conditions until further use. 5% (w/v) alginate (Alg) solution was prepared by slowly adding the Alg powder to DI water at room temperature under stirring condition (500 rpm, 2 h). The clear solution obtained was then stored at 4° C. until further use. To prepare the gel, a polymer blend of MC and Alg was prepared by mixing them at the volume ratio of 1:1. The concentration of $CaCl_2$) (0.3% w/v) in MC was adjusted so that the liquid-like behavior of the blend at lower temperature would not be affected by the crosslinking between Alg and $CaCl_2$. When subjected to 37° C., the blend transformed to gel within 15 min of incubation. 20 mg of MPs were introduced to the polymer blend before gelation and dispersed uniformly to develop the MPs-gel scaffolds (FIG. 1, Scheme 1).

Measurement of Viscoelastic Property

Parallel plate rheometer (RDA III, Rheometric Scientific) was used to measure the rheological properties of gel only and MPs-gel scaffolds. Dynamic viscoelastic parameters such as dynamic shear storage modulus (G') and loss modulus (G") were measured as a function of angular frequency at 37° C. The gel was formed on a glass plate and transferred within the space between two parallel metal plates. The top plate was lowered to a gap distance of 0.6 mm and a frequency sweep test from 0.1 to 100 rads at 20% strain amplitude was performed.

Incorporation and Release of Growth Factors

BMP-9 and VEGF were incorporated to the MPs-gel scaffolds to promote the bone regeneration. The release of these growth factors was tailored by incorporating BMP-9 to the MPs and VEGF to the gel enabling a temporal release profile. The BMP-9 was incorporated non-covalently to the MPs through a passive absorption process. 20 mg of MPs were immersed in 500 ng of BMP-9 solution and incubated at 4° C. for complete absorption. Equal amount of MPs were immersed in sterile PBS and incubated at 4° C. to prepare the non-coated MPs. These MPs were incorporated to the polymer blend before the gelation. 1 µg of VEGF was directly added to 0.5 ml polymer blend and mixed properly before gelation. The final concentration of BMP-9 and VEGF on the MPs-gel was thus 1 µg/ml and 2 µg/ml, respectively. Three groups of the MPs-gel were prepared, indicated as MPs-gel (without any growth factors), MPs-gel+V (with VEGF only), and MPs-gel+V+B (with VEGF and BMP-9 coated MPs).

The release of BMP-9 from the coated MPs, and both BMP-9 and VEGF from MPs-gel+V+B, was evaluated. ELISA based detection was used for the quantitation of released BMP-9 and VEGF. For release studies, coated MPs only or MPs-gel+V+B were placed in a glass vial and 2 ml of 1× sterile PBS was added to the vials which were then subjected to 37° C. on an orbital shaker set to 50 rpm. At predetermined time points (1 h, 3 h, 5 h, day 1, day 3, day 5, day 7, and day 14), the PBS from the vial was collected and replaced with fresh PBS. The collected PBS was stored at −20° C. before performing the ELISA. The remaining amount of BMP-9 was determined by dissolving the MPs on acetic acid, and the remaining amount of VEGF on MPs-gel+V+B was determined by dissolving the gel in cold water at the end of the release study. The release profile is presented as a percent cumulative release based on the total amount present on MPs and MPs-gel+V+B scaffolds.

Biological Activity of BMP-9

The characterization of BMP-9 was done in terms of its effects on cytotoxicity, proliferation, and differentiation of hMSCs on a 24 well plate (2-D culture) and within the MPs-gel system (3-D culture). Prior to studies with MPs-gel, the bioactivity of BMP-9 coated on the MPs was determined by evaluating the attachment and proliferation of hMSCs and rat MSCs (rMSCs) on the surface of MPs. rMSCs were harvested from the femur bone marrow of rats.

2-D Culture System

Human bone marrow derived mesenchymal stem cells (hMSCs) were expanded 3 to 4 times on serum-free media (StemPro XenoFree supplemented with GlutaMAX). To study the effects of BMP-9 on cell viability and proliferation, hMSCs were harvested from the culture dishes and seeded to the 24 well plate at the density of 20,000 cells/well with DMEM complete media containing MSC qualified FBS and penicillin/streptomycin. BMP-9 was added to the cells at the concentration of 0, 10, and 100 ng/ml. During each media change, new BMP-9 was added to the fresh media to maintain the required concentration of BMP-9. At day 3 and 7, live and dead cell assay was performed and the qualitative analysis of viability and proliferation of hMSCs was performed using fluorescence imaging.

The osteogenic differentiation of hMSCs on 2-D culture was studied using ALP quantification and alizarin red staining. The concentration of BMP-9 was maintained at 100 ng/ml for the cells seeded at the density of 30,000 cells/well. For ALP quantification, the cells were grown in four different groups as normal medium (NM) with and without BMP-9 as well as osteogenic medium (OM) (normal medium supplemented with 10 nM dexamethasone, 50 µM ascorbic acid, and 10 mM β-glycerol phosphate) with and without BMP-9. At day 3 and 7, ALP assay was performed to quantify the ALP activity. The cells on the well were washed with PBS followed by the addition of 250 µl of lysis buffer and kept under shaking condition for 2 min. The lysed cell suspension was collected, centrifuged, and the supernatant was mixed with p-nitrophenyl phosphate (pNPP) substrate, and the kit instructions were followed. The ALP activity was normalized with the total protein content of the sample which was determined using Coomassie Plus protein assay kit (ThermoFisher Scientific, MA). To further study the mineralization induced by the osteogenic differentiation, Alizarin red staining was performed at day 14. The cells were fixed with 2.5% buffered glutaraldehyde and washed with PBS. The washed cells were left for staining with the Alizarin red solution for 15 min and washed again with DI water a few times. The staining of calcium mineral deposits was observed under color bright field microscopy.

3-D MPs-Gel System

Prior to the cell studies with MPs-gel system, the bioactivity of BMP-9 coated on the surface of MPs was determined. MPs coated with BMP-9 were seeded with the hMSCs and rMSCs at the density of 20,000 cells per 20 mg MPs in a 24 well plate. Species-specific BMP-9 was used for hMSCs and rMSCs. To increase the contact between the cells and MPs, 200 µl of cell suspension was first added to MPs and incubated for 3 h followed by the addition of remaining 800 µl of media. At day 3 and 7, the MPs from the cell seeded well were transferred to a new well and washed with PBS. The qualitative analysis of attachment and viability of MSCs growing on MPs was performed using live/dead assay kit. After confirming the bioactivity of BMP-9 coated on the MPs, a series of in vitro studies was performed to determine the in vitro osteogenic properties of the MPs-gel system.

Seeding and Viability of hMSCs within MPs-Gel

50 µl of cell suspension containing 40,000 hMSCs was added to the MPs-polymer blend (0.5 ml) on glass chamber slides and incubated at 37° C., 5% $CO_2$ for 30 min. The polymer blend with MPs underwent gelation forming MPs-gel with hMSCs encapsulated within it. 1 ml complete culture medium was added to the chambers and returned to the incubator. 500 µl of medium was removed every three days and replaced with the same amount of fresh medium. At day 3 and 10, live and dead cell assay was performed. The culture medium was removed from the chamber slides and the MPs-gel was washed with PBS. Live and dead cell stain diluted in DPBS was added directly to the chamber and incubated for 30 min. Confocal microscopy was performed to qualitatively observe the viability of hMSCs encapsulated within the MPs-gel. To maintain the stability of gel during imaging, the temperature of the microscope chamber was maintained at 37° C.

In Vitro Osteogenic Differentiation

ALP activity of the cells within the MPs-gel was determined to study the osteogenic differentiation of encapsulated hMSCs. $10^5$ hMSCs were cultured in the presence of OM and half amount of OM was replenished every 3 days. To liberate the encapsulated cells, MPs-gel was flash frozen by immersing in liquid nitrogen followed by its pulverization. The disrupted powder was transferred to the lysis buffer and the similar process as explained was followed to quantify the ALP activity at day 7 and 14. To further observe the calcium deposition within the MPs-gel, at day 10, MPs-gel were processed into histological slides embedded in paraffin and von kossa staining was performed. Briefly, the slides were first deparaffinized by immersing in a series of xylene, 100% and 30% ethanol and washed thoroughly with DI water. Silver nitrate solution was added to the washed slides placed on an aluminum foil, and the slides were illuminated with a 60 W bulb for 20 min. The slides were washed again and observed under bright field microscopy.

Gene Expression Study

An osteoblast specific gene expression study was performed at day 7 and 14 with the cells cultured in the presence of OM. To isolate the RNA from the encapsulated cells, MPs-gel samples were flash frozen in liquid nitrogen and pulverized. The pulverized powder was added to the Trizol reagent (VWR International, PA) for the RNA isolation followed by its purification using RNeasy kit (Qiagen Group, USA). The purified RNA was quantified using Nanodrop-1000 spectrophotometer (ThermoFisher Scientific, MA). The RNA amount for the reverse transcription into complementary DNA (cDNA) was done based on the lowest concentration of RNA among the samples and cDNA synthesis kit (Verso kit, ThermoFisher Scientific, USA) was used for cDNA synthesis following the manufacturer's instruction. The early osteogenic markers such as ALP and collagen 1 (Col1) as well as late marker such as osteocalcin (OCN) were analyzed. Quantitative reverse transcription polymerase chain reaction (RT-PCR) was performed using SYBR green qPCR kit (Smart Biosciences, USA) and StepOne Plus thermal cycler (Applied Biosystems, CA). The obtained Ct values for the target genes were normalized using GAPDH as the housekeeping gene and the fold change for MPs-gel+V and MPs-gel+V+B was expressed relative to the MPs-gel only group.

Animal Studies

All the animal tests were conducted with the approval from the Institutional Animal Care and Use Committee (IACUC) at the University of Toledo. Eight-week old male rats (Charles River laboratories, MA) were anaesthetized using isoflurane inhalation (2-3% isoflurane vaporized in 02). The anaesthetized rats were maintained at 1.5% isoflurane for both injection and surgery procedures.

Ectopic Bone Formation

Rats were divided into three groups (n=5) based on the scaffold composition. MPs-gel, MPs-gel+V+B, and MPs-gel+V+B with osteoinduced rMSCs (cultured with OM for 5 days) were loaded to 1 ml syringe and kept on ice until injection. Two injections of the same group of scaffold per rat were done to the subcutaneous pocket using 13 G needle Immediately after injection, the rats were transferred to the recovery chamber and housed individually after recovery.

After 2 and 4 weeks post-injection, the rats were sacrificed and the MPs-gel with surrounding tissues were harvested. For histological analysis, the harvested tissues were fixed in 10% (v/v) neutral buffered formalin, dehydrated in sequentially increasing ethanol solutions to 100% (v/v) ethanol, immersed in xylene, and embedded in paraffin. The tissue samples were cross-sectioned to 5 µm thickness and stained with hematoxylin-eosin (H&E), Masson's Trichrome to observe the bone tissue formation. The tissue samples after 4 weeks were harvested with the outer skin and subjected to dual-energy X-ray absorptiometry (DEXA) before performing the histological analysis. Since the shape of the new tissue was different for different samples, total bone mineral content (BMC) on new tissue was determined and reported instead of bone mineral density (BMD).

Cranial Bone Formation

Animal Surgery

The surgical site was shaved and disinfected with a series of isopropanol, betadine scrub, and betadine solution. An 0.8 mm incision was made along the midline of skull and the periosteum was set aside to expose the bone. Two full circular defects of 3.5 mm diameter were created, using a micro-drill and burr, on the calvarium of each rats. The defect site was regularly flushed with sterile saline to remove the bone debris and minimize the heat production during drilling. Each defect was injected with 0.2 ml of MPs-gel. The study groups were divided into a void group, MPs-gel group, and MPs-gel+V+B group with each group consisting of 5 animals (total 10 defects per group). The animals were euthanized at 12 weeks post-operation and the bone formation along the defects was analyzed using micro-computed tomography (microCT).

MicroCT and Histological Evaluation

The bone samples harvested from the rats were positioned in a 34 mm diameter specimen holder and scanned using a microCT system (µCT100 Scanco Medical, Bassersdorf, Switzerland). Scan settings were: voxel size 18 µm, 70 kVp, 114 µA, 0.5 mm AL filter, and integration time of 500 ms. Analysis was performed using the manufacturer's evaluation software, and a fixed global threshold of 21% (210 on a grayscale of 0-1000) was used to segment bone from non-bone. A cylinder the width of the skull with a diameter of 3.5 mm and centered over the defect was analyzed.

The harvested bone samples were decalcified for a week before they were embedded in the liquid paraffin for sectioning. 5 µm thick sections were fixed on the microscope slides for staining with H&E.

Statistical Analysis

The statistical analysis was performed using SPSS software. Two-tailed paired sample test t tests were performed to evaluate gene expression. Analysis of variance (ANOVA) followed by Tukey's post hoc analysis was performed to test the significance between the groups. A value of $p<0.05$ was considered significant.

Results and Discussion

Synthesis of MPs and MPs-Gel

CS MPs prepared using coacervation technique by cross-linking with TPP have been used in many drug delivery and tissue regeneration applications. Spherical MPs with the size ranging from 300 to 1000 µm can be fabricated using this technique where the drops of CS solution are dripped to the TPP solution under stirring condition. The size of the MPs fabricated using air drying technique in these examples ranged from 600 µm to 700 µm. These MPs were difficult to inject using 13 or 16 G needles due to their size. These air dried MPs were further rinsed in water under stirring condition and then again air dried. This process provided a reduced size of the MPs, namely, 500 µm to 600 µm. This reduced size made the MPs easier to inject using 13 or 16 G needles.

The MC solution itself undergoes gelation at higher temperature depending on the molecular weight. MC used in these examples at the concentration of 10% (w/v) has been reported to have a gelation temperature of 40.1° C. through calorimetry experiments. Increasing the concentration beyond 10% may reduce the gelation temperature and bring it more towards the physiological temperature. However, such solutions are more difficult to handle due to high viscosity. Another method to lower the gelation temperature is through the addition of salts, but it has been shown to reduce the strength of the gel when subjected to aqueous or cell culture environment.

Figure 2:
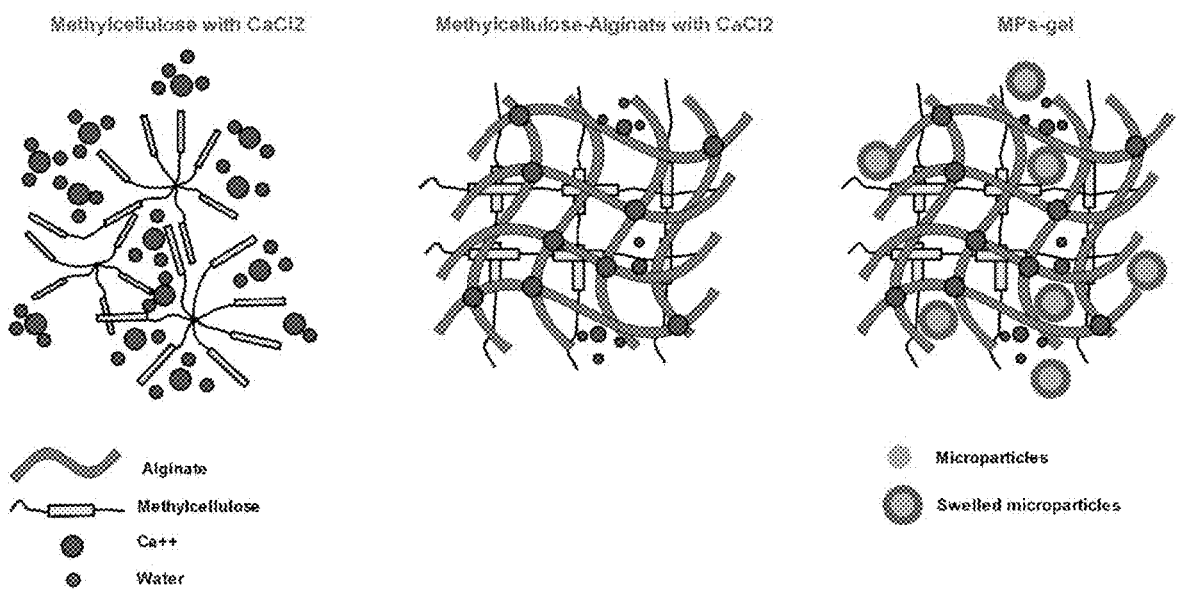
FIG. 2: Scheme 2, showing gelation of methylcellulose (MC), MC-alginate (MC-Alg), MPs-gel at 37° C. The MPs within the gel are in swelled form, which causes a faster gelation of the MC-Alg blend.

In these examples, a gel that can undergo gelation at 37° C. with better gel strength was developed. A strategy of blending two polymers and blended MC with calcium chloride and Alg was used to prepare the composition. This polymer blend formed a strong crosslinked gel at 37° C. (FIG. 2, Scheme 2). It slightly lost the liquid-like flow after blending due to the crosslinking between Alg and calcium chloride, and was more of semi-liquid at lower temperature. But when subjected to 37° C., the composition formed a gel within 15 min of incubation. This gel was developed as an injectable medium for MPs so that a good retention of MPs could be achieved at the injection or defect site.

Figure 3A:
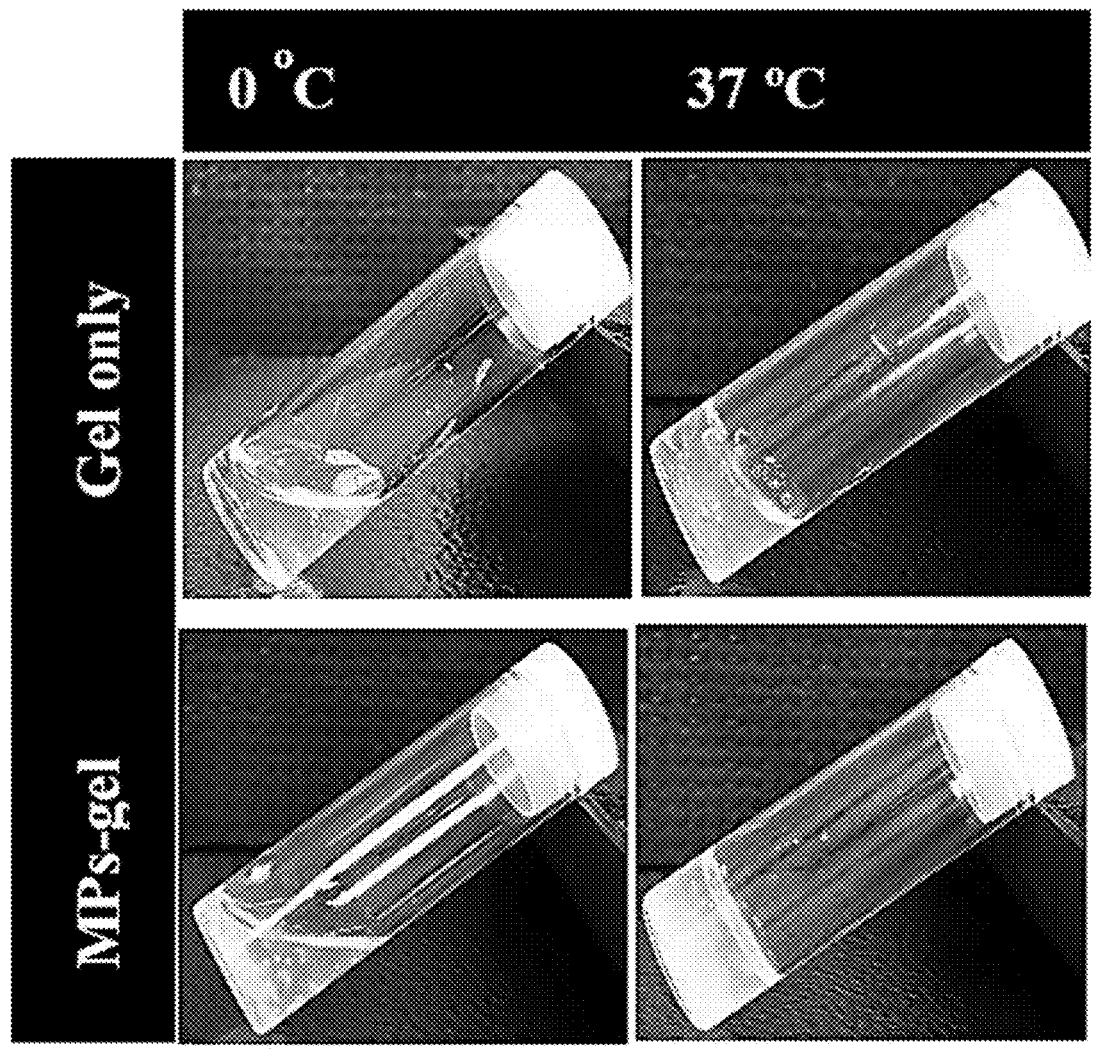
FIGS. 3A-3E: Physical appearance (FIG. 3A), FTIR analysis spectra (FIG. 3B), and rheological property of gel and MPs-gel (FIG. 3C) at 0° C. and 37° C.
Figure 3B:
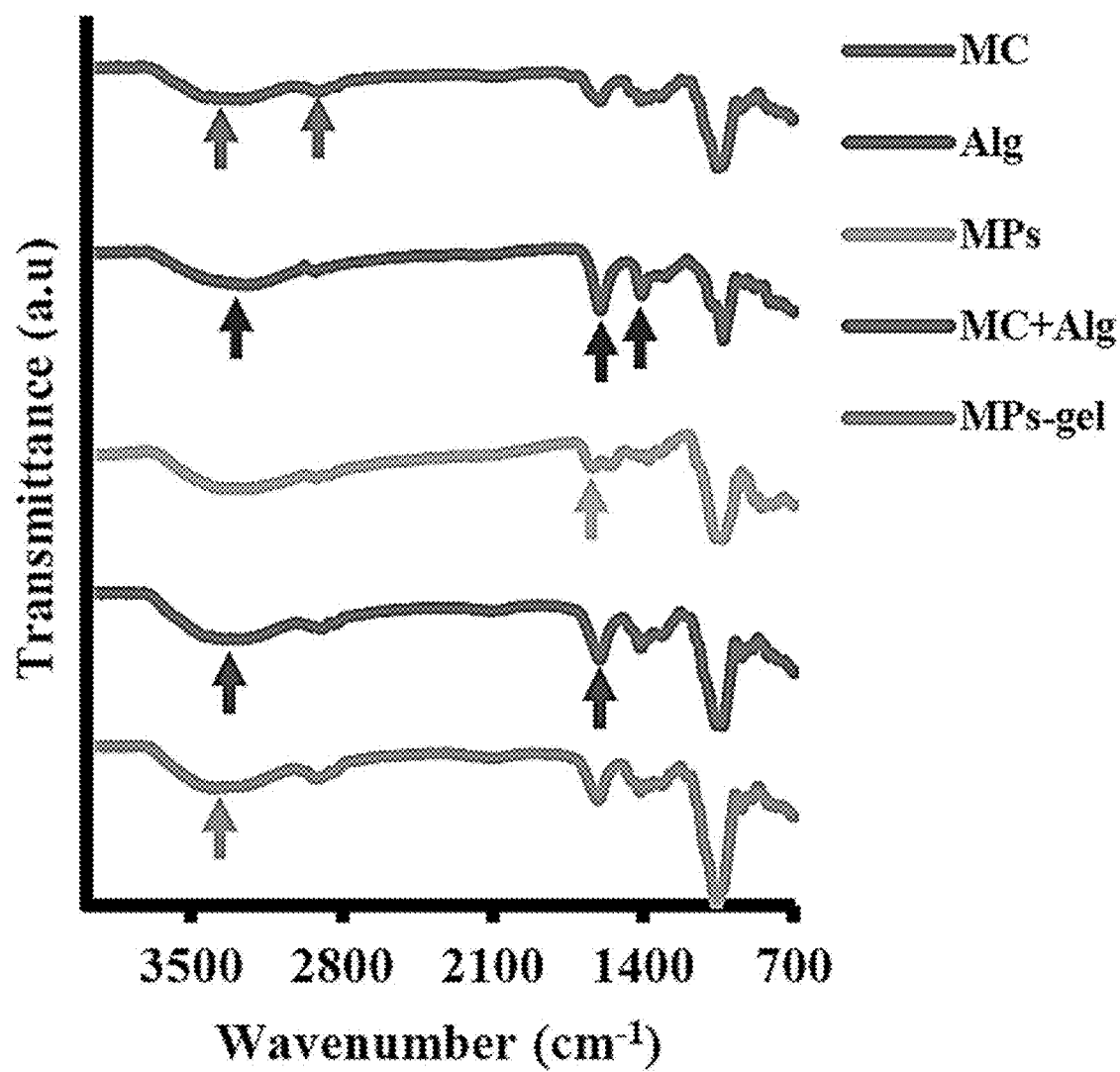
Figure 3C:
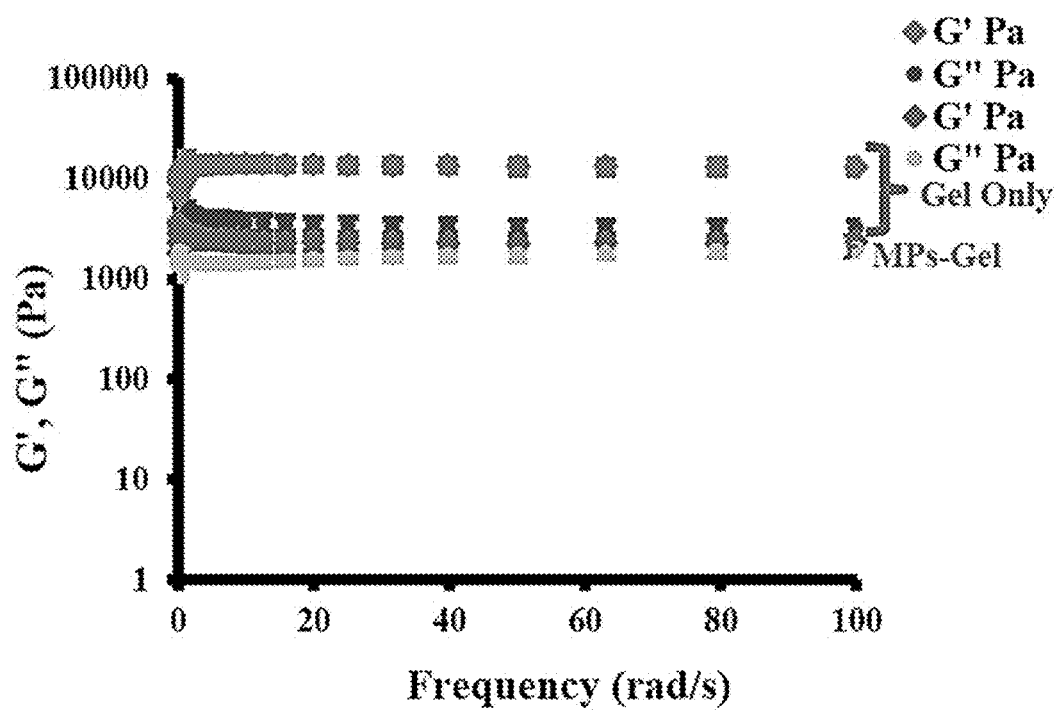
Figure 3D:
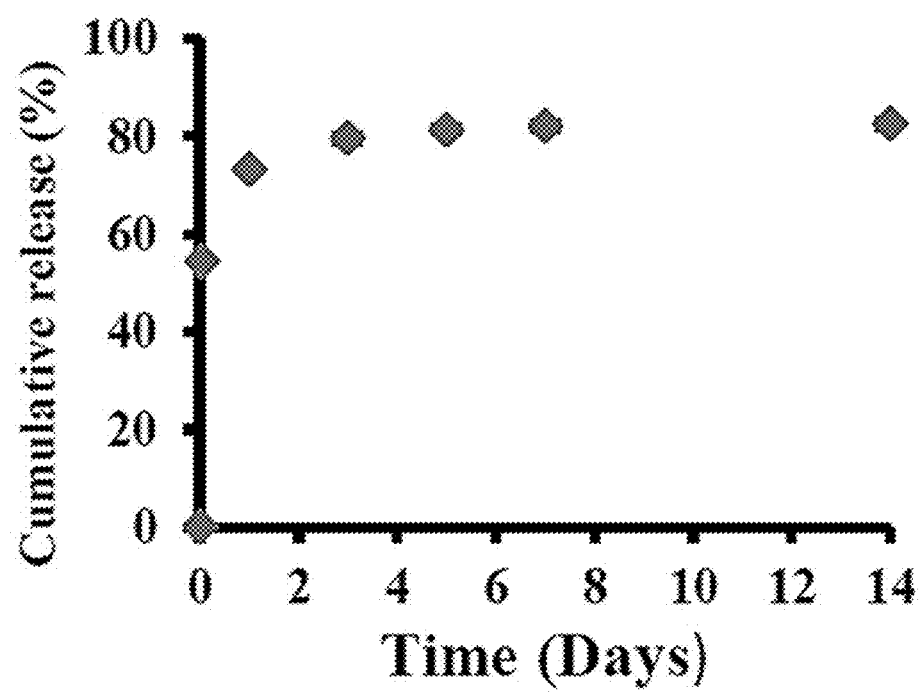

Furthermore, the release of BMP-9 coated on the MPs can be controlled from the MPs-gel system due to the additional diffusion barrier presented by crosslinked gel. The gelation of the polymer blend was not affected by the addition of MPs; instead, faster gelation was observed with MPs-gel compared to only gel (FIG. 3A). This is due to the absorption of water by MPs from the blend solution as a result of which the viscosity increases faster. This was qualitatively confirmed as the MPs were observed to be swelling within the gel. The FTIR analysis (FIG. 3B) showed the characteristic peak of MC at 3426 cm-1 (O—H stretching) and 2903 $cm^{-1}$ (C—H stretching in $CH_2$ and $CH_3$). The characteristic peaks of Alg were observed at 1599 $cm^{-1}$ and 1406 $cm^{-1}$, corresponding to the asymmetric and symmetric stretching of COO—, respectively. The O—H stretching peak for Alg was observed at 3248 $cm^{-1}$. The peak at 1634 $cm^{-1}$ in MPs spectrum corresponds to the shifted amide I band in CS. The polymer blend of MC and Alg showed the O—H stretching peak at 3298 $cm^{-1}$, which was shifted to lower value compared to MC and higher value compared to Alg. This peak was slightly narrow compared to that observed in Alg. Without wishing to be bound by theory, it is believed that these changes may be due to the interaction of Ca with Alg and a result of polymer blending. There was no change in peak position of asymmetrical stretching of COO— observed at 1599 $cm^{-1}$, which is normally observed in calcium alginate complexes. The spectrum of MPs-gel showed all the peaks observed in MC-Alg blend except that the O—H stretching peak was shifted to 3420 $cm^{-1}$ with slight peak broadening. This indicates that introduction of MPs to the blend increased the hydrogen bonding as evidenced through the swelling of MPs when introduced to the blend.

Viscoelastic Property of Gel

The frequency sweep test for gel only and MPs-gel was performed at 37° C. using parallel plate rheometer. The result in FIG. 1C shows that G' (storage modulus) remains almost constant at higher frequencies for both gel only and MPs-gel. This indicated the stiff nature of gel and that the gel will remain stable over the period of time. This is one of the important properties required for the injectable gel. The G" (loss modulus) also followed the similar pattern for both samples. The actual magnitude of G' and G" for MPs-gel system was lower than that for gel only samples. The gelation of MC at higher temperature occurs due to the formation of intra- and inter-molecular chain hydrophobic interaction. The strength of MC based gel thus is due to the formation of hydrophobically cross-linked network. In these examples, the ionic interaction between negatively charged group in Alg and $CaCl_2$) also contributes to the overall strength of the gel. The addition of MPs, however, lowers this ionic interaction as CS itself can undergo ionic complexation with negatively charged groups. This may have resulted in the lower strength of MPs-gel scaffolds compared to gel only.

Release of BMP-9 and VEGF

The delivery system plays an important role in determining the efficacy of BMPs based treatments. The necessary dose of this protein to induce bone formation may be significantly decreased, if the protein can be retained at the intended site for an extended period of time in a bioactive form. The release of BMP-9 from coated MPs was demonstrated first. Considering the physical absorption of BMP-9 on the surface, the release was first believed to be a burst, but, surprisingly, the result showed that more than 70% of BMP-9 was released within 24 h (FIG. 1D). It has been reported that encapsulation of BMPs into microparticles can slow down their release, but the problems with the lower encapsulation and the requirement of harsh chemical treatments significantly affects the bioactivity of BMPs. Furthermore, the use of MPs only to study their bone forming ability in in vivo models such as ectopic bone formation is virtually impossible as they cannot be localized at specific site. In these examples, these burst-releasing coated MPs were used as a BMP-9 carrier incorporated to an injectable gel. However, surprisingly, the gel acted as a reservoir to control the release of BMP-9 while also protecting it from in vivo degradation.

Figure 3E:
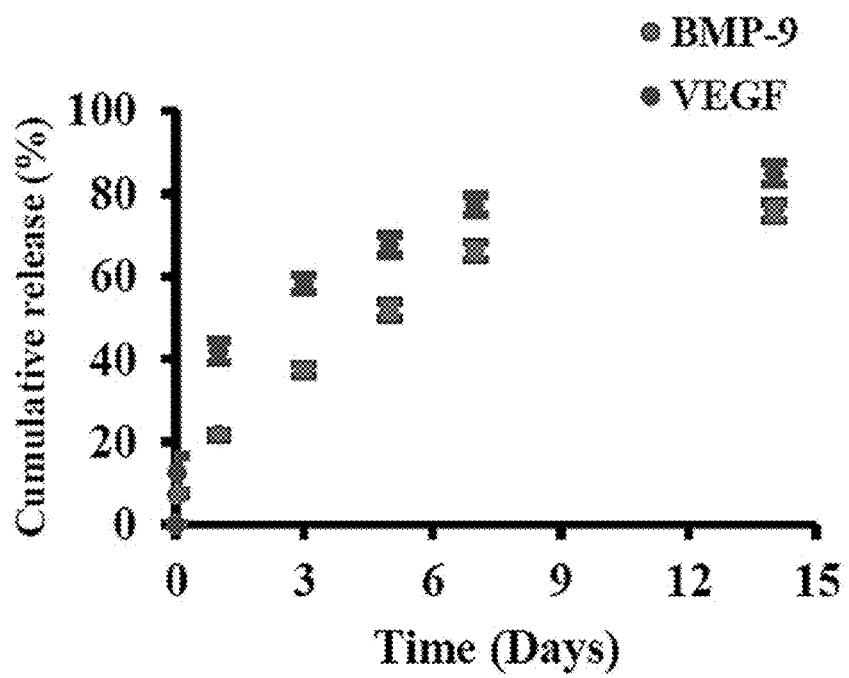

The coated MPs were incorporated into the polymer blend containing VEGF. VEGF is a key regulator of angiogenesis during the bone formation process. Angiogenesis involves the formation of new blood vessels from pre-existing blood vessels. During the normal bone healing process, the expression of VEGF is high during earlier time points followed by the expression of BMPs later. The example MPs-gel system was developed to have a similar temporal release profile with faster and more VEGF release in the earlier days. After 24 h, about 40% of VEGF was released from MPs-gel compared to 20% BMP-9 release. The release of BMP-9 from MPs-gel was thus slower and less than the VEGF release. Also, it was more controlled than the burst release from MPs only (FIG. 3E). The slower release of BMP-9 from MPs-gel system increases its bio-availability within the gel, which is especially advantageous when the hydrogel encapsulates cells such as stem cells.

In Vitro Bioactivity of BMP-9 in 2-D Culture

While BMP-2 and BMP-7 have shown ability in a series of clinical trials both in spine and orthopedic trauma, it is not known if these are the most effective BMPs for the promotion of fracture healing. Endogenous BMP-9, however, may be the most osteogenic among all BMPs. Studies done with hMSCs transfected with BMP-9 expressing adenovirus have shown to significantly improve the ALP expression by hMSCs even at the low concentration of expressed BMP-9 (600 μg/ml). Very few studies done with recombinant BMP-9 have shown that the addition of BMP-9 to 2-D culture of pre-osteoblasts and adipose derived stem cells results in a significant improvement of osteogenic activity of these cells. The potent osteogenic activity of BMP-9 has been attributed to the fact that BMP-9 is resistant to BMP antagonist noggin, which generally inhibits the BMP induced SMAD signaling pathways. The studies showing the osteogenic potential of recombinant BMP-9 were performed mostly with pre-osteoblasts, and the studies involving BMP-9 and hMSCs were done mostly with adenovirus transfection.

Figure 4A:
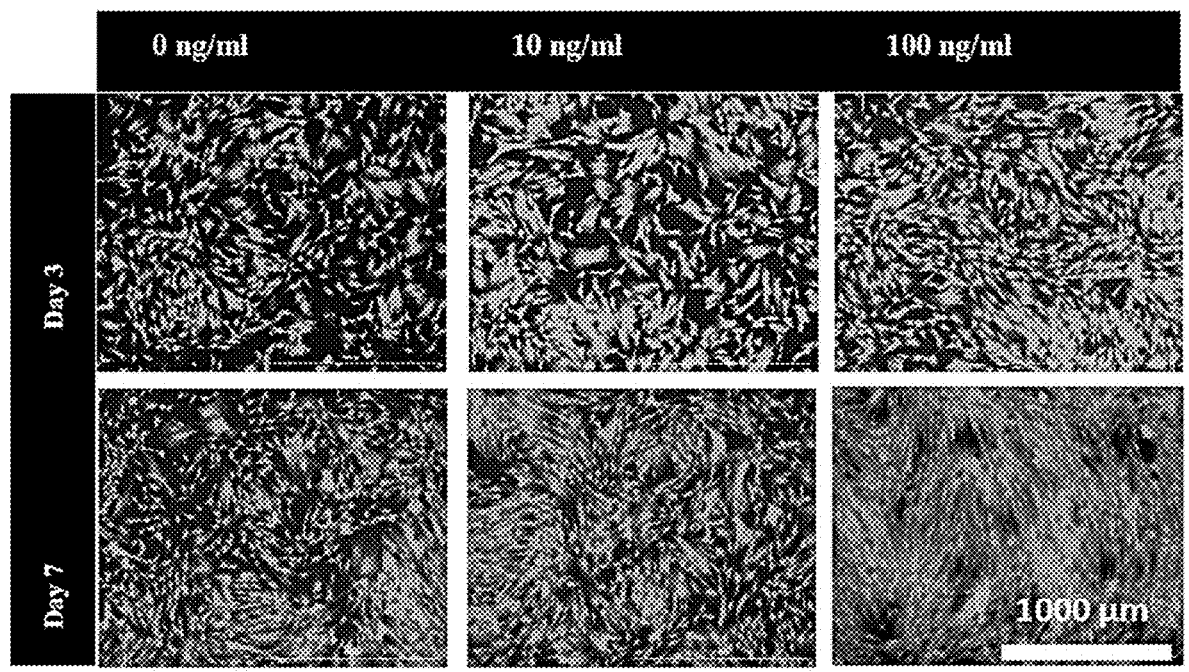
FIGS. 4A-4C: Human mesenchymal stem cells (hMSCs) growth and proliferation at different concentration of BMP-9 (FIG. 4A).
Figure 4B:
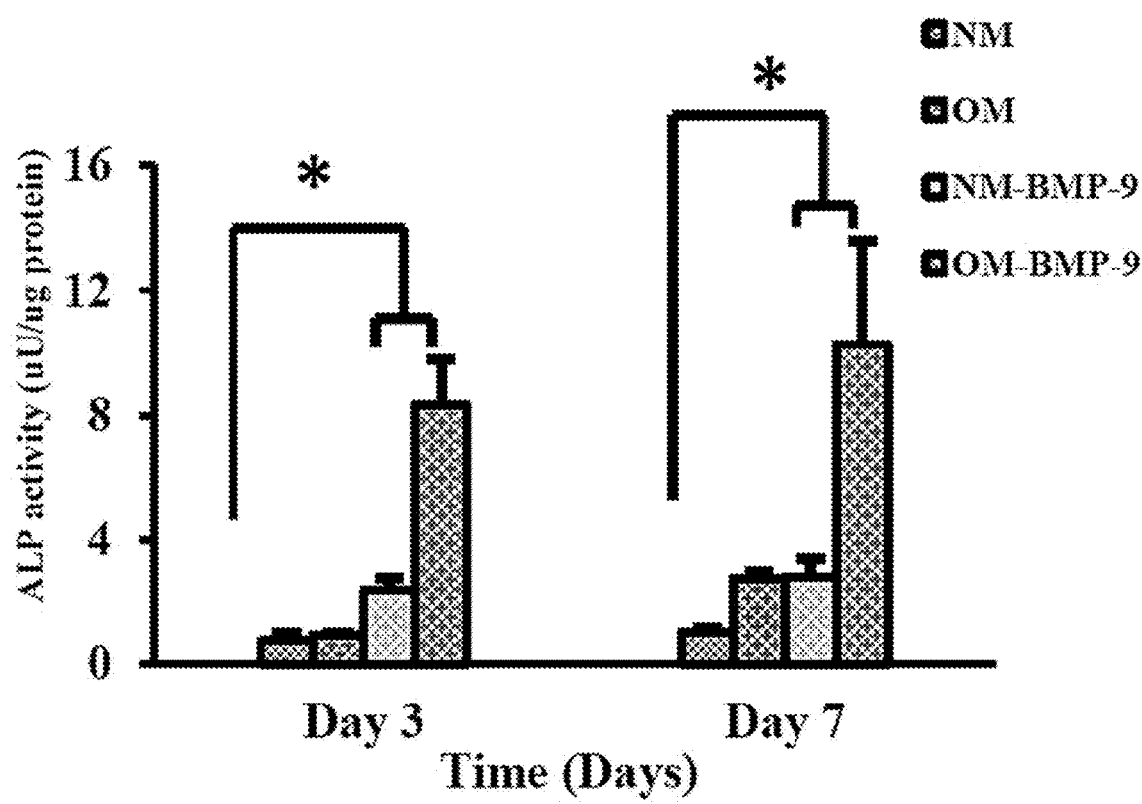

In order to study the therapeutic level and osteogenic activities of recombinant BMP-9 with hMSCs, these examples utilized two different concentrations of BMP-9 and characterized the effects in terms of toxicity, proliferation, and differentiation of hMSCs in 2-D culture. As shown in FIG. 4A, the addition of BMP-9 to the 2-D culture of hMSCs at two different concentrations improved their proliferation without causing any toxic effects. Qualitatively, higher proliferation was observed with 100 ng/ml concentration at both day 3 and 7. ALP expression study was performed to study the osteogenic differentiation of hMSCs in 2D culture at BMP-9 concentration of 100 ng/ml and in the presence of normal medium (NM) and osteogenic medium (OM). The results in FIG. 4B show that at both day 3 and 7, osteogenic differentiation of hMSCs in the presence of BMP-9 was taking place both with NM and OM, indicated by the higher expression of ALP. The ALP expression was comparatively lower in the absence of BMP-9. At day 7, the scenario slightly changed with significantly high differentiation of hMSCs in the presence of BMP-9 and OM. The cells growing with BMP-9 in NM and only OM had similar ALP activity, which was significantly higher than that with NM only. The result here shows the ability of BMP-9 to induce the early osteogenic differentiation of hMSCs even without the osteogenic supplements. The osteogenic differentiation, however, is best achieved with BMP-9 in the presence of OM as indicated by significantly higher expression of ALP with this group.

Figure 4C:
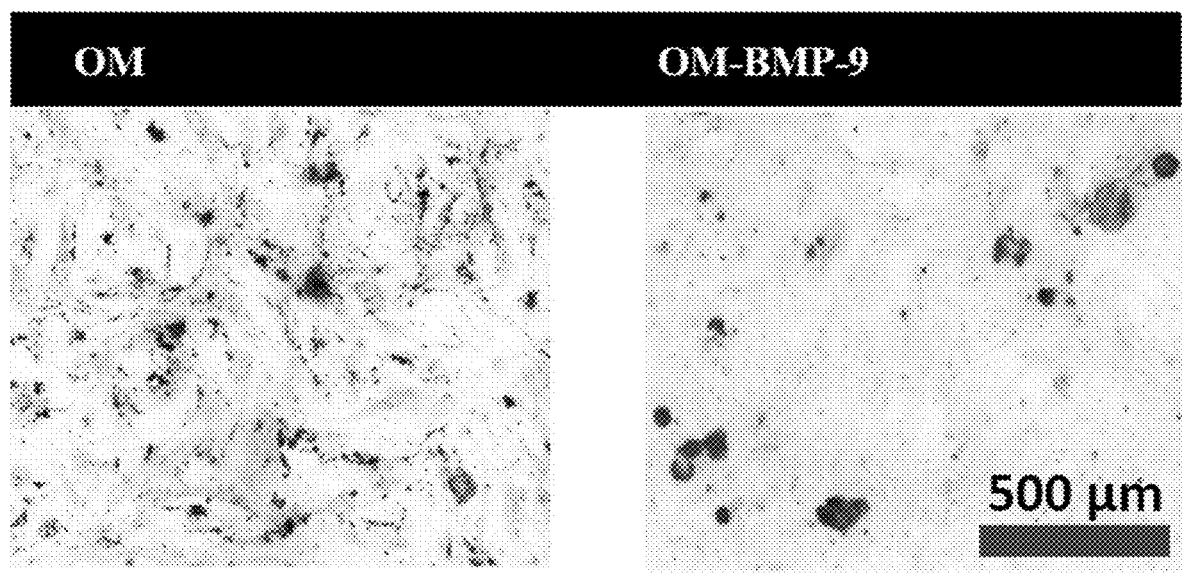

The mineralization induced by the osteogenic differentiation was evaluated using alizarin red staining at day 14 for the hMSCs with BMP-9 (100 ng/ml) and without BMP-9 in OM. As shown in FIG. 4C, the mineralized deposits were present in both groups indicated by the presence of red spots across the well. It was qualitatively observed that these deposits were denser and more uniform along the whole surface area of the well containing BMP-9 when compared to that without BMP-9 where deposits were observed in few areas. This result is consistent with the ALP expression data, where osteogenic differentiation was higher for hMSCs grown in OM with BMP-9. The overall results here show the significant ability of BMP-9 to induce the osteogenic differentiation of hMSCs in 2-D culture.

In Vitro Bioactivity of BMP-9 Coated MPs

Figure 5A:
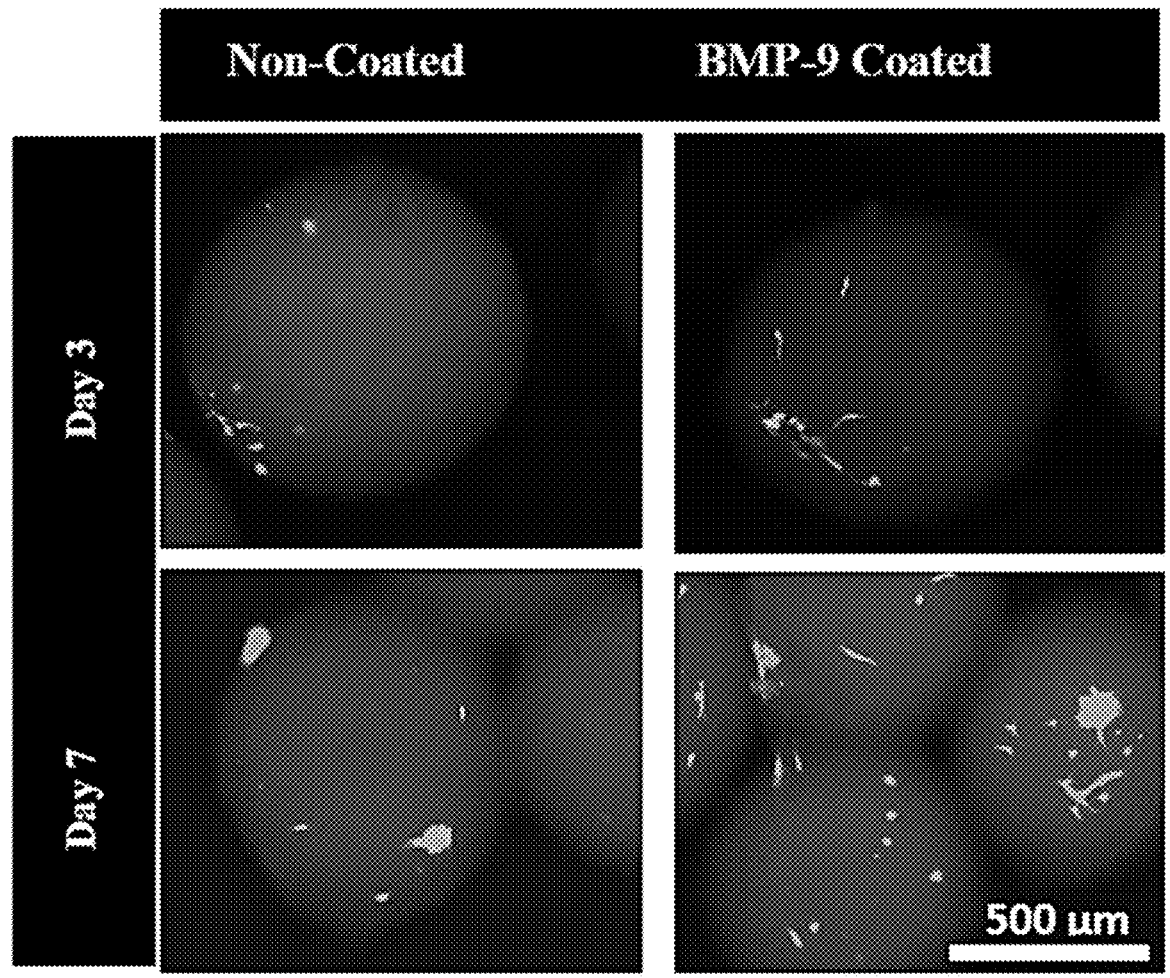
FIGS. 5A-5G: In vitro response of hMSCs and rMSCs in MPs and MPs-gel scaffolds.
Figure 5B:
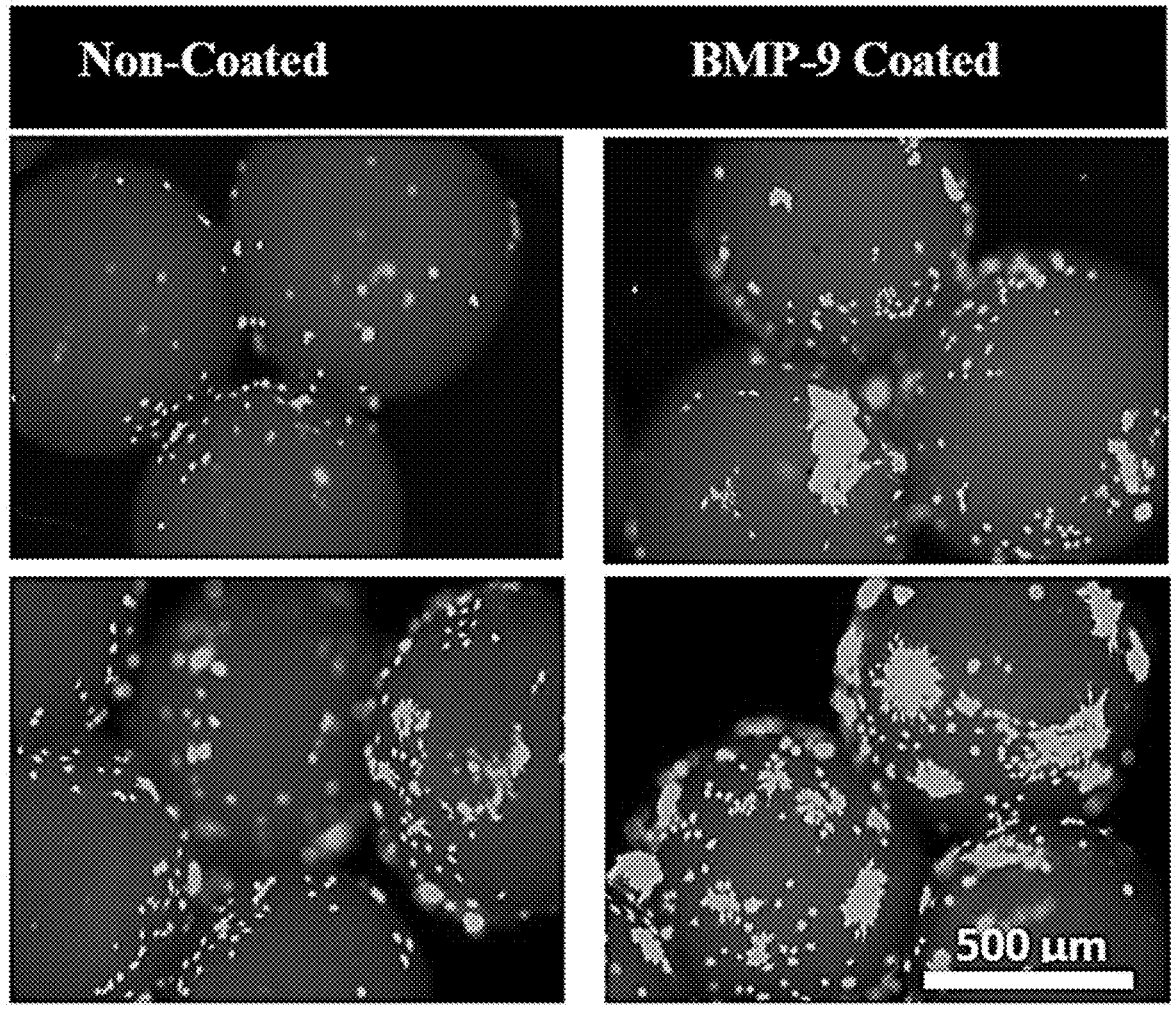

The osteogenic response of BMP-9 combined with VEGF delivered through MPs-gel was studied. As a first step, the bioactivity of BMP-9 coated on the MPs was determined in order to analyze the ability of CS MPs to be used as BMP-9 carriers. The CS MPs were prepared in very mild conditions without the use of harsh chemical treatment. The direct physical absorption of BMPs, though results in the bulk release quickly, has been previously shown to improve their bioactivity compared to direct grafting to the materials. Bioactivity of coated BMP-9 was studied by observing the attachment and proliferation of hMSCs and rMSCs on the MPs. The results (FIGS. 5A-5B) showed that the attachment and proliferation of MSCs at both day 3 and 7 was higher on BMP-9 coated MPs than on non-coated MPs. The cells on coated MPs grew on big colonies along the surface. The rMSCs growth (FIG. 5B) was denser than that of hMSCs (FIG. 5A) which may be due to the larger size of hMSCs and the curvature of the MPs limiting their attachment to the MPs. The results, however, showed that the BMP-9 coated on the surface of MPs was bioactive and enhanced the attachment and proliferation of MSCs.

In Vitro Response of MPs-Gel Scaffolds

Figure 5C:
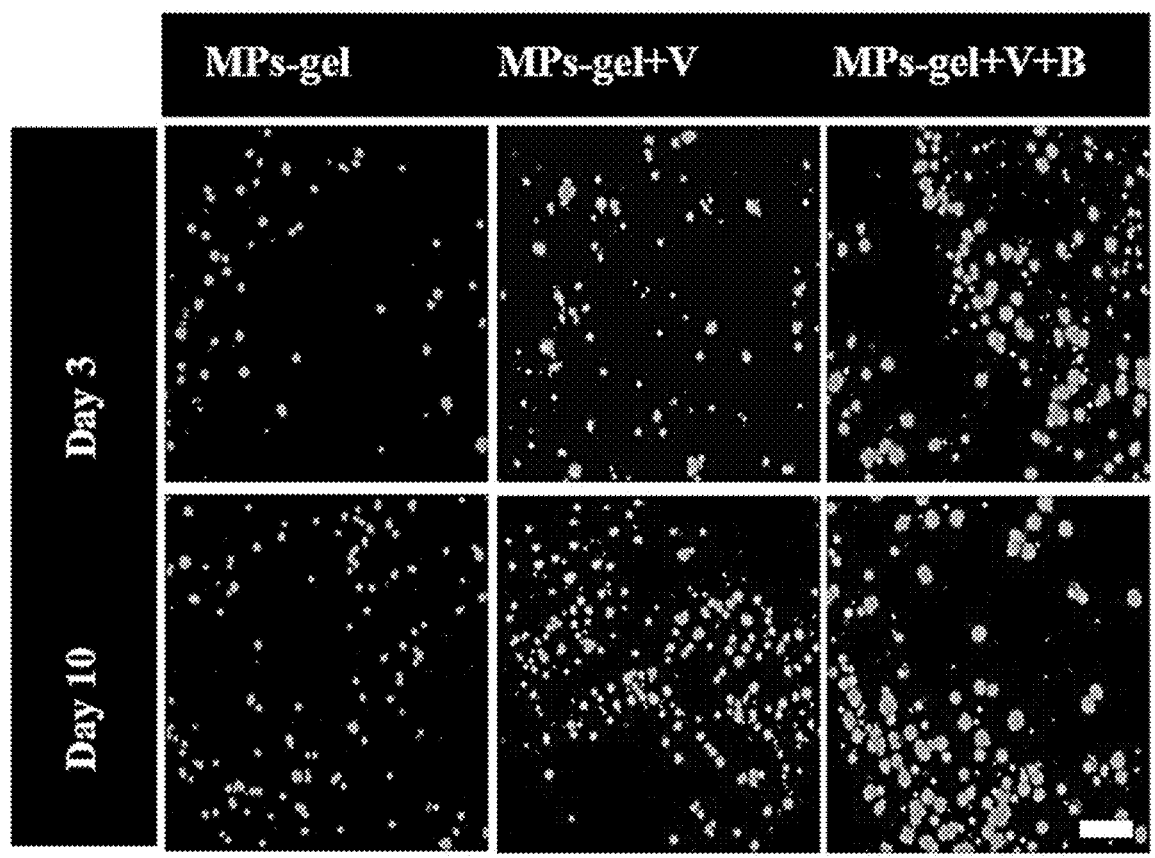

The osteogenic response of BMP-9 combined with VEGF delivered through MPs-gel was evaluated. All of the polymers used in the development of MPs-gel scaffolds were naturally derived with established biocompatibility properties. While CS and Alg have been shown to have excellent cytocompatibility, MC may have a differing response to the cells depending on molecular weight (MW). In general, polysaccharides with high MW are less cytocompatible compared to those with low MW. The MC used in these examples has been shown to have an excellent response to the cells. The viability of hMSCs encapsulated within the MPs-gel system is shown in FIG. 5C. The MPs-gel system maintained an excellent cell viability up to 10 days of encapsulation, shown by green fluorescence with a sparse number of dead cells indicated by the red/yellowish fluorescence. The cells mostly stayed with the spherical morphology on all groups of MPs-gel with significantly less spreading at both days. Furthermore, there was no qualitative differences in the cell proliferation among different groups of MPs-gel. This shows the very minimal role of BMP-9 in stimulating the MSCs elongation and proliferation in a 3-D gel. Indeed, it has been previously shown that the proliferation of MSCs during bone formation is mostly dominated by TGF-β1 and other pathways. The combined effects of TGF-β1 and BMP-9 was able to induce MSCs proliferation in the early stages of cell cycle. Furthermore, the fact that BMP-9 can stimulate the osteogenic differentiation of MSCs during the early stages may implicate its minimal role in their proliferation. The results here show the ability of MPs-gel to encapsulate the MSCs and maintain their long term viability. It was observed that both BMP-9 and VEGF have a non-significant role on improving the hMSCs proliferation within the developed gel.

Figure 5D:
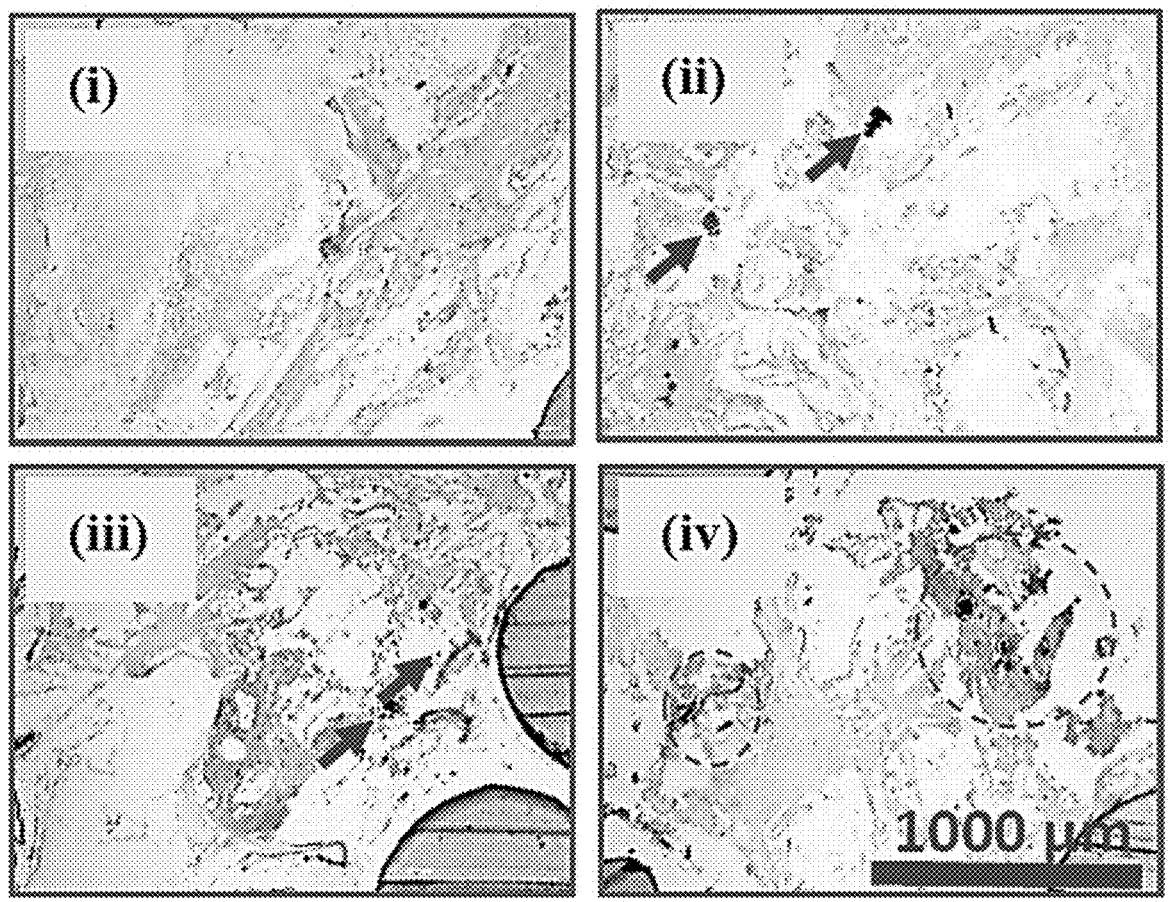
Figure 5E:
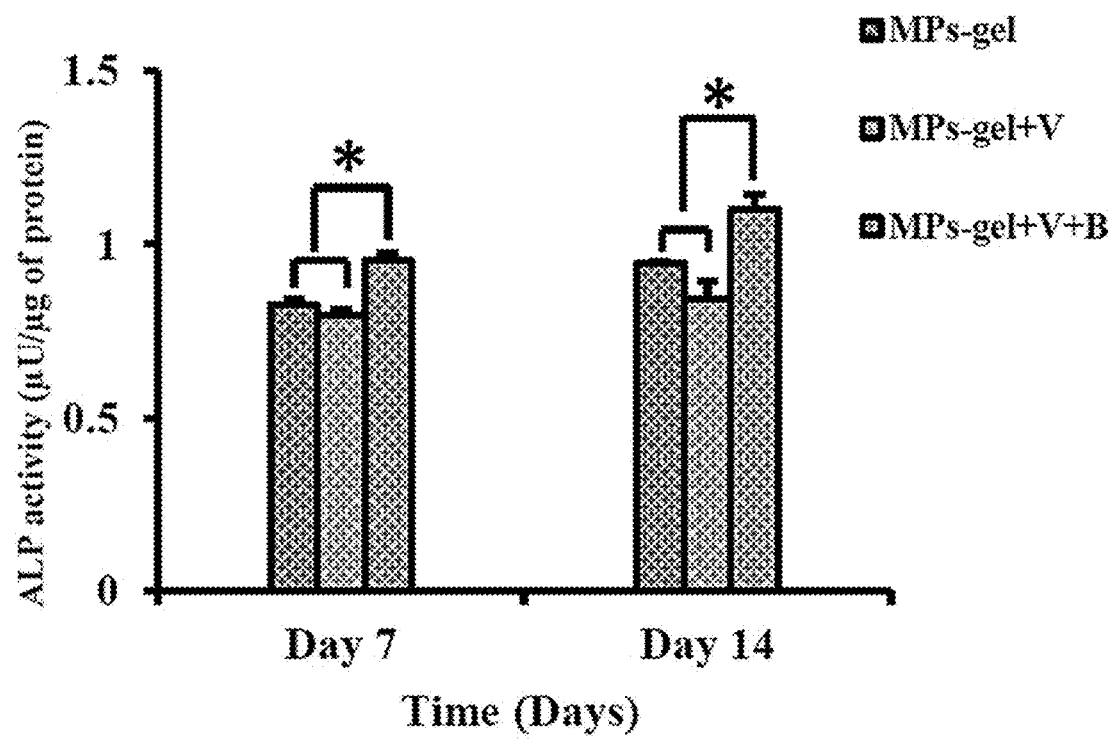

The differentiation of encapsulated hMSCs to the osteogenic lineage within the MPs-gel system was examined to evaluate the osteoinductive ability of BMP-9 on a 3-D culture system, where their different adhering and limited stretching pattern compared to on a 2-D culture system was observed. Very few studies have reported the ability of recombinant BMP-9 to promote in vitro osteogenic differentiation in semi-rigid 3-D gel matrix, whereas there are many studies showing the ability of BMP-9 to enhance the ALP expression by MSCs and pre-osteoblasts through adenoviral transfection in 2-D and rigid 3-D culture environment. Results here showed that the ALP expression (FIG. 5E) by the cells cultured within MPs-gel+V+B was significantly higher ($p<0.05$) than other groups at both time points. The expression of ALP by cells within the MPs-gel with and without VEGF was almost similar, indicating that VEGF itself had no role to directly influence the osteogenic differentiation of hMSCs. Mineral deposition is one of the important events that takes place during the osteogenic differentiation. The calcium deposits within the MPs-gel were observed using Von kossa assay at day 14 after processing the MPs-gel-cell construct into the histological slides. As shown in the microscopy images in FIG. 5D, there were not any black deposits on the MPs-gel samples without any hMSCs. The samples encapsulating hMSCs showed some mineral deposition, indicated by the black dots on the images, showing the onset of mineralization within the gel by differentiated cells. Comparatively, the black deposits were more visible on the MPs-gel+V+B and were present over the larger surface area than that on the MPs-gel and MPs-gel+V.

Figure 5F:
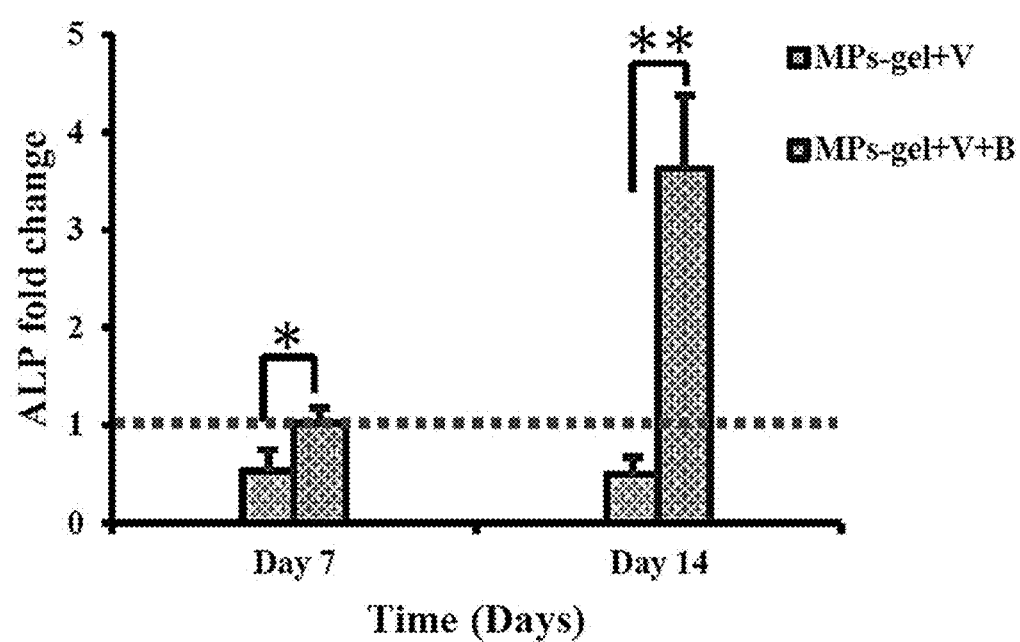
Figure 5G:
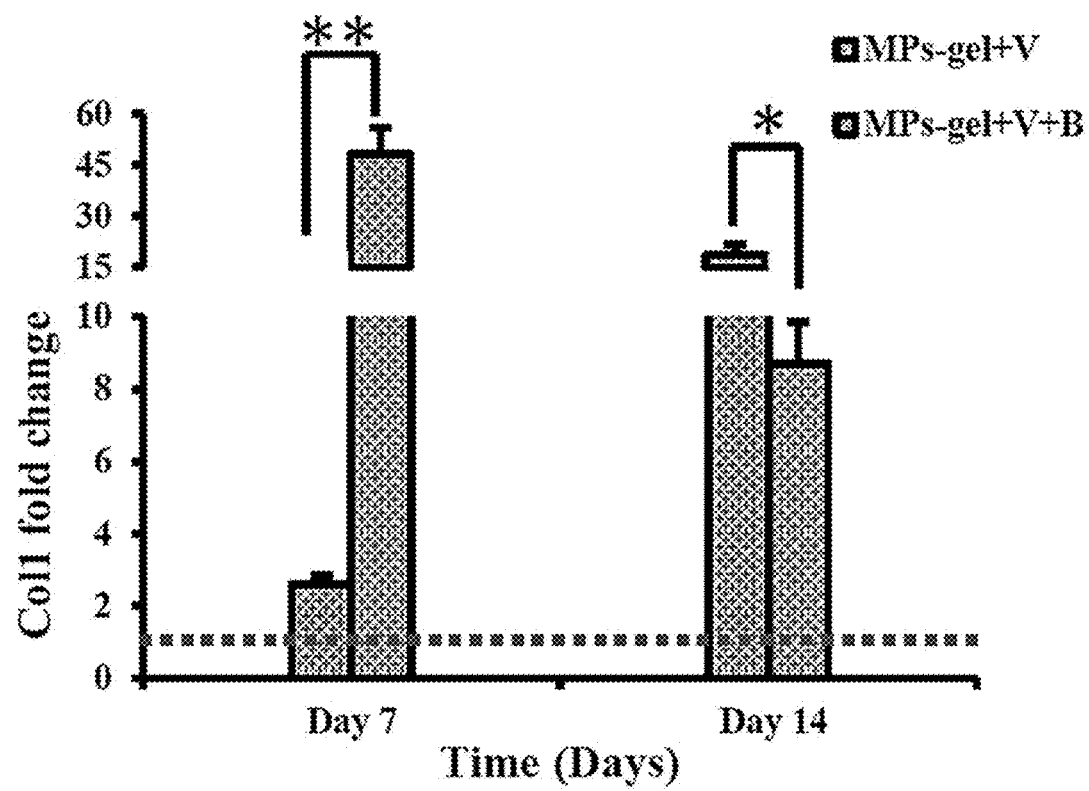
Figure 5H:
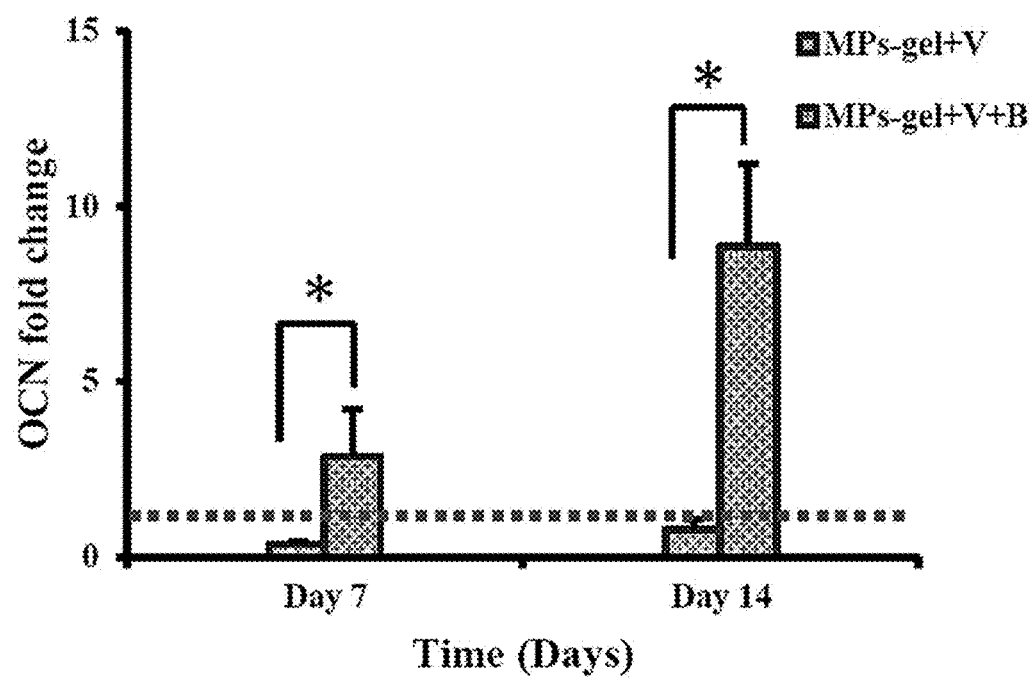

Osteogenic differentiation of MSCs is accompanied by the upregulation of osteogenic genes expression. In these examples, three specific genes pertinent to bone development and mineralization were focused on. ALP and Col1 are relatively early markers of osteogenic differentiation. The expression of these genes shows the early osteoblasts lineage commitment of MSCs. Col1 is a major inorganic component of bone extracellular matrix. OCN, on the other hand, is a relatively late marker whose expression is accompanied by the matrix mineralization. OCN is mainly secreted by the mature osteoblasts and is one of the most abundant non collagenous proteins of the extracellular matrix. The fold changes in expression of genes by MPs-gel+V and MPs-gel+V+B are expressed relative to the expression of genes by the MPs-gel group. As shown in FIG. 5F, MPs-gel+V+B upregulated the expression of ALP on both day 7 and 14 while that by MPs-gel+V was slightly downregulated compared to MPs-gel group on both days. The expression of Col1 was significantly upregulated on MPs-gel+V+B group on day 7 (FIG. 5G). Interestingly, the expression of Col1 on day 14 was decreased, however the expression of OCN was upregulated (FIG. 5H). Thus, the group containing BMP-9 showed significant differences in the expression of all three genes, demonstrating the ability of BMP-9 to induce the osteogenic differentiation of MSCs within 3-D gel. The results here show that BMP-9 can not only significantly improve the osteogenic differentiation of MSCs in 2-D culture, but also in a 3-D gel. Both early and late osteogenic differentiation markers were significantly upregulated in BMP-9 containing groups. The mechanism of BMP-9's potent osteogenic ability is not currently known. Without wishing to be bound by theory, it is believed that all osteogenic BMPs' except BMP-9 induced osteogenic differentiation is inhibited by Noggin, a common antagonists for other BMPs. Results have also indicated that BMP-9 induced bone formation is also resistant to BMP-3, which is another potent antagonist to BMPs.

Ectopic Bone Formation

Figure 11:
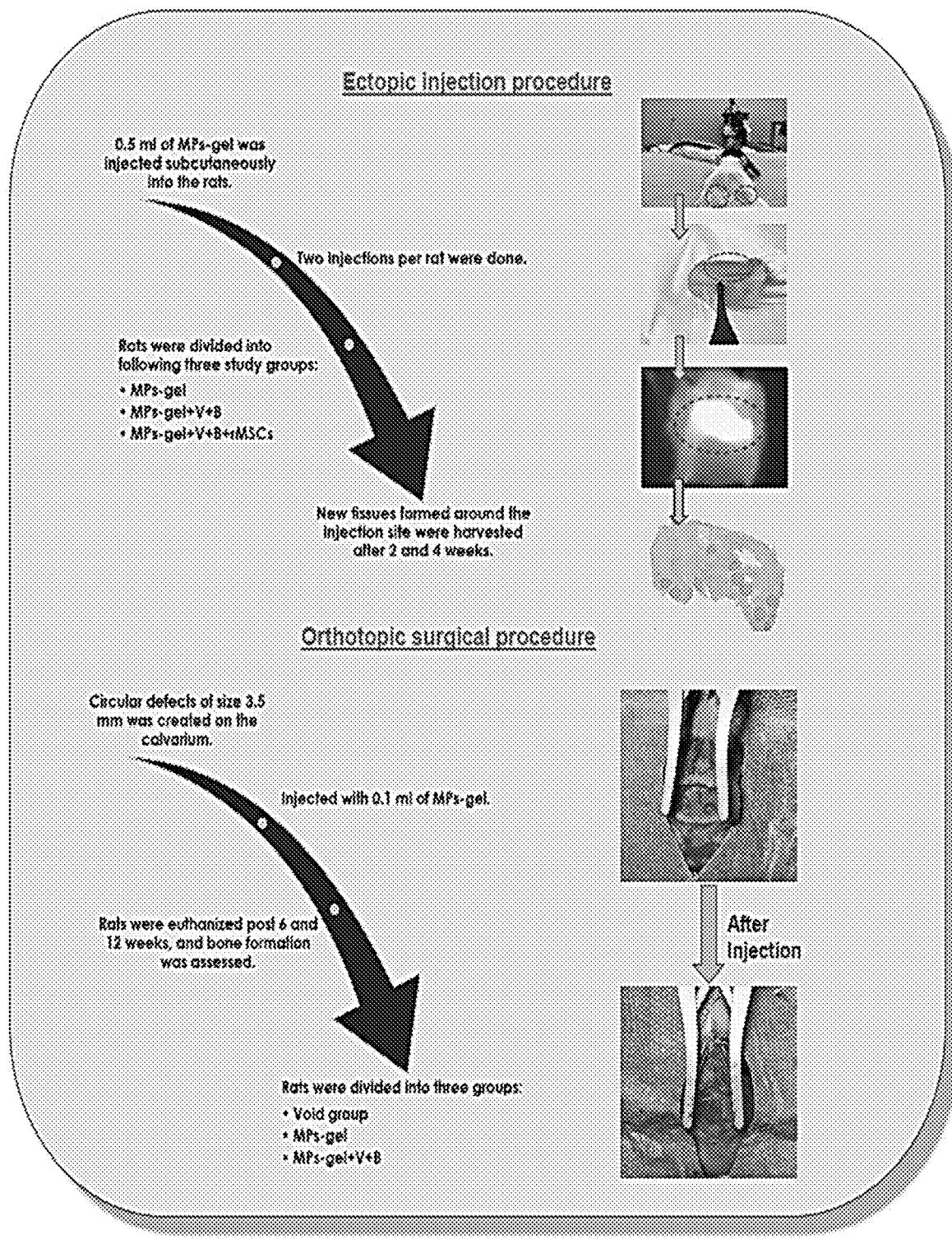
FIG. 11: Illustration showing ectopic injection and orthotopic surgical procedures utilized in the examples herein.

The subcutaneous bone formation in rodents was evaluated as it allows to test if the developed system can support bone formation while eliminating the effect of bone-stimulating cytokines, bone forming cells, and potentially bone-stimulating mechanotransduction. FIG. 11 shows an illustration summarizing the process utilized. Many studies have shown the ability of BMP-9 to induce the ectopic bone formation. However, almost all such studies utilized osteoprogenitor cells or stem cells of different origin transduced with BMP-9 expressing viral vectors. Recombinant proteins, on the other hand, provide a safer, reliable, and established alternative to study protein induced processes.

Figures 6A, 6B, 6C, 6D, 6E, 6F, 6G:
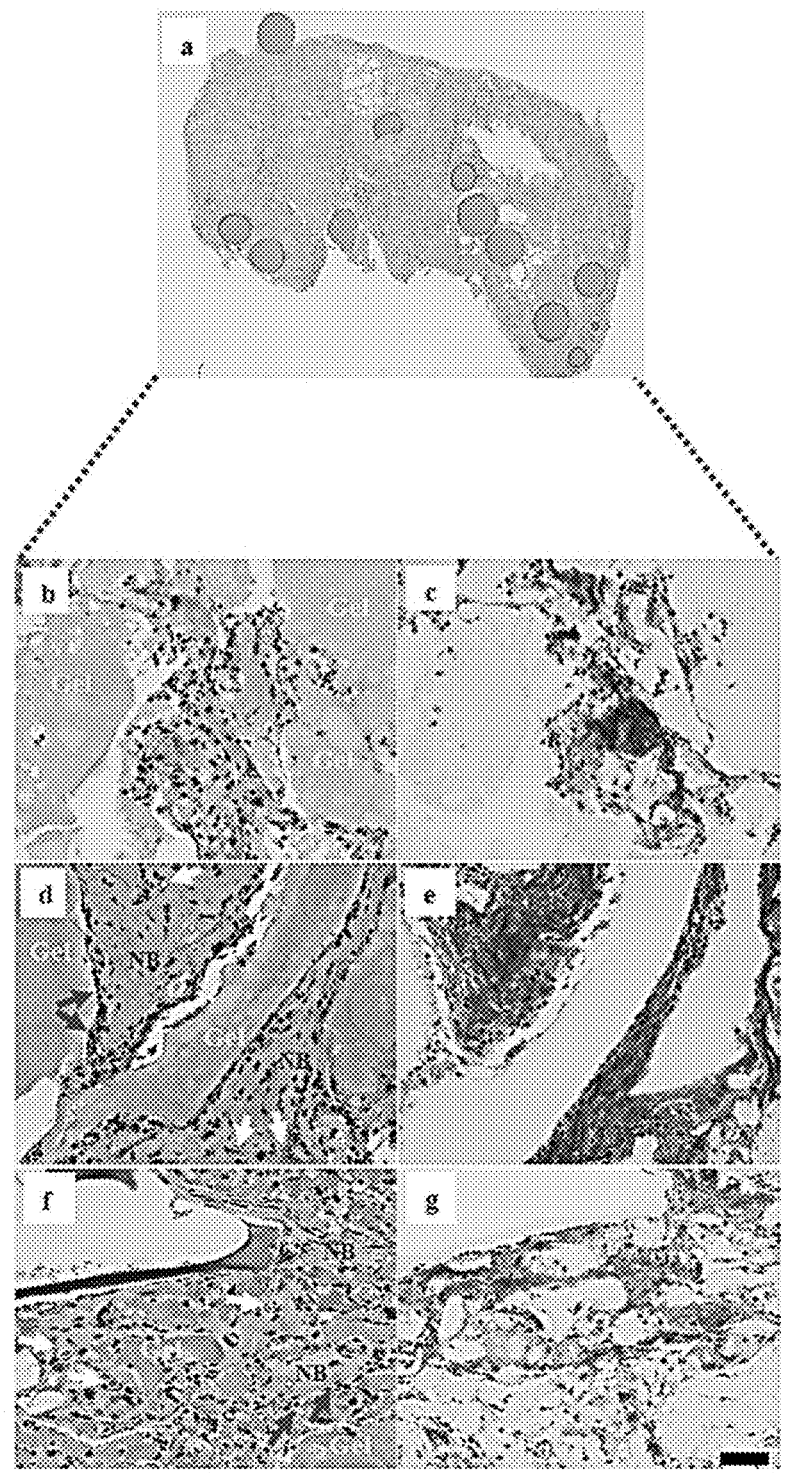
FIGS. 6A-6G: Histological sections stained with H&E and Masson's trichrome stains to show the subcutaneous bone formation in rats after 4 weeks. The top section shows the localization of MPs within the harvested tissue after 4 weeks of injection (FIG. 6A). The left and right panels show the H&E and Masson's trichrome sections respectively for MPs-gel (FIGS. 6B, 6C), MPs-gel+V+B (FIGS. 6D, 6E), and MPs-gel+V+B with hMSCs (FIGS. 6F, 6G).

The results herein show subcutaneous bone formation induced by the BMP-9 incorporated thermoresponsive gel. In order to specifically study the role of BMP-9 and VEGF within MPs-gel, the samples injected included MPs-gel, which was more of a control group for MPs-gel+V+B and MPs-gel+V+B+osteoinduced rMSCs. The group with rMSCs was included to study if those cells would accelerate the ectopic bone formation process. It was observed that all groups of injected MPs-gel were well retained within the subcutaneous injection site and bonded well to the subcutaneous tissues. It was also observed that MPs remained with gel at the injection site, indicating the gel was able to retain the MPs at the target site (FIG. 6A). After 4 weeks, MPs-gel+V+B with cells were noticeably more rigid and larger in size when compared to other two groups and appeared more resistant to deformation during isolation and handling. FIGS. 6B, 6C show the representative H&E and Masson's trichrome stained sections, respectively, for the tissue samples harvested from MPs-gel. At 2 weeks the gel structure mostly remained intact with the huge infiltration of fibroblasts. At 4 weeks, the gel seemed to be degrading away and dispersed collagen fibers were present, shown by the pink stains in FIG. 6B and blue stains in FIG. 6C. There was, however, no evidence to support that these collagenous materials were remodeling into bone as indicated by the absence of osteoblast like cells and blood vessels.

Figure 6H:
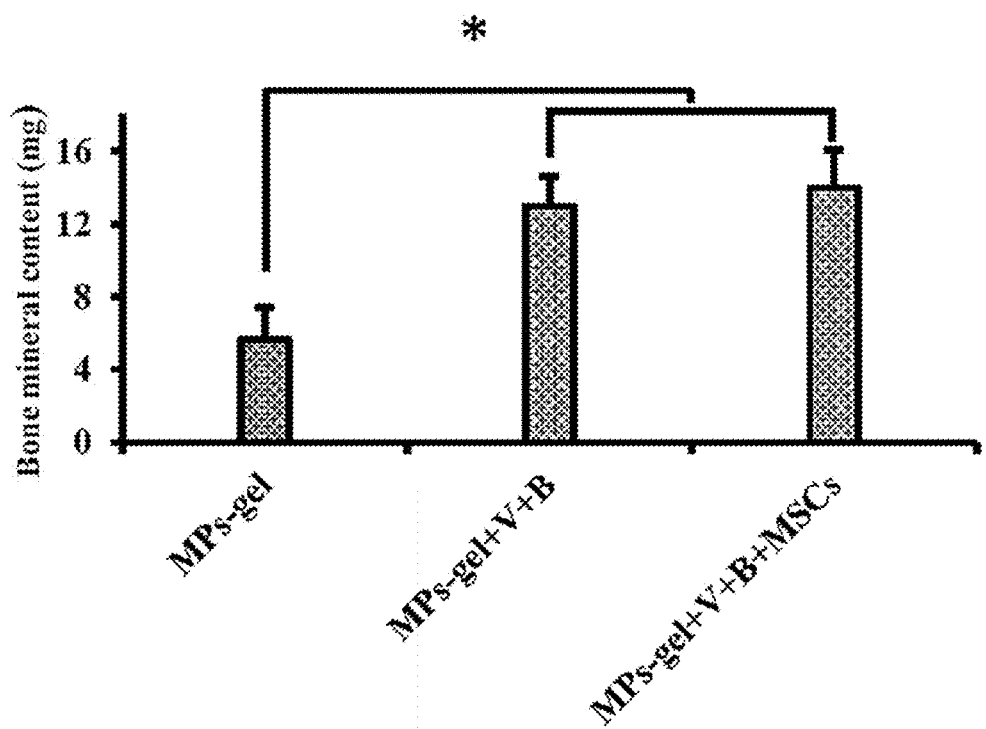
FIG. 6H shows total bone mineral content quantified using DEXA for the tissue harvested after 4 weeks. (NB: new bone).

The samples harvested from MPs-gel+V+B showed the new bone formation. The areas of new bone were lined with osteoblasts and abundant new blood vessels were present. The result from MPs-gel+V+B with rat MSCs was similar to that without cells with areas of new bone formation observed across the section. The blood vessels were also present abundantly on these samples. FIG. 6H shows the quantification of bone mineral content (BMC) measured using dual energy X-ray absorptiometry (DEXA). The results show the significantly higher BMC value ($p<0.05$) for the experimental groups compared to MPs-gel group, indicating the role of growth factors in bone formation. There was no significant difference in BMC values between MPs-gel+V+B and MPs-gel+V+B+MSCs. This indicates that the rapid infiltration of cells into MPs-gel occurred at the ectopic site, enabling the bone formation to occur without the need of exogenous cells.

The representative stained sections of tissue sample harvested from MPs-gel+V+B are shown in FIG. 6D and FIG. 6E. This group showed the presence of fibrous collagenous tissue at 2 weeks, indicating the onset of ectopic bone formation. The role of VEGF was evident through the presence of abundant blood vessels. At 4 weeks, the woven bone-like structure was evident throughout the harvested tissue. They were found to be lined with osteoblasts (red arrows), and the blood vessels continued to form along these structures. This indicates that BMP-9 was able to induce ossification within the multiple site of the MPs-gel and VEGF induced neo-vascularization.

Another experimental group included MPs-gel+V+B with $1\times10^6$ rMSCs derived from the femoral bone marrow of 3 week old rat. This group was included to study if the ectopic bone formation due to MSCs in MPs-gel+V+B would be different than without MSCs. Previous studies have shown that the ectopically injected or implanted scaffolds with MSCs show better bone formation than with only BMPs. Qualitatively, it was observed that the tissue sections harvested from this group were larger in size compared to those from other groups. Fibrous collagenous materials were present with abundant blood vessels at 2 weeks. At 4 weeks (FIGS. 6F-6G), woven bone structures were observed lined with osteoblasts. The onset and remodeling of ectopic bone formation at 2 and 4 weeks on this group were similar to that without MSCs except the presence of bone structure on more regions of harvested tissue on this group.

The subcutaneous bone formation was further investigated by measuring BMC using DEXA. The results show the significantly higher mineral content in MPs-gel+V+B and MPs-gel+V+B+MSCs group compared to MPs-gel group (FIG. 6H). This further shows the ability of BMP-9 and VEGF to induce the ectopic bone formation within a month of injection. There was no significant difference in mineral content between the growth factor loaded groups with and without cells. The similar results with and without MSCs indicate that the host cells can rapidly infiltrate into the MPs-gel where they are eventually differentiated to the bone forming osteoblasts. BMP-9 delivered with VEGF through MPs-gel, thus, can induce the subcutaneous bone formation in the absence of bone forming cells.

Cranial Defects

Figure 7A:
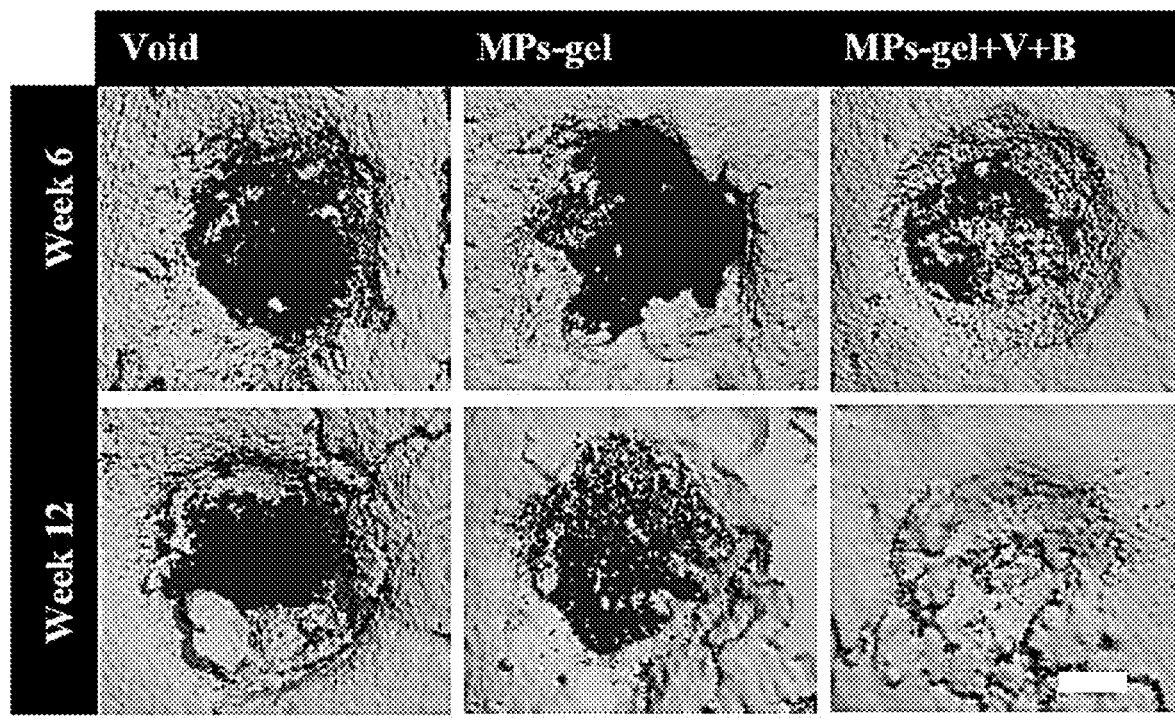
FIGS. 7A-7C: MicroCT evaluation of bone formation on cranial defects of rats.
Figure 7B:
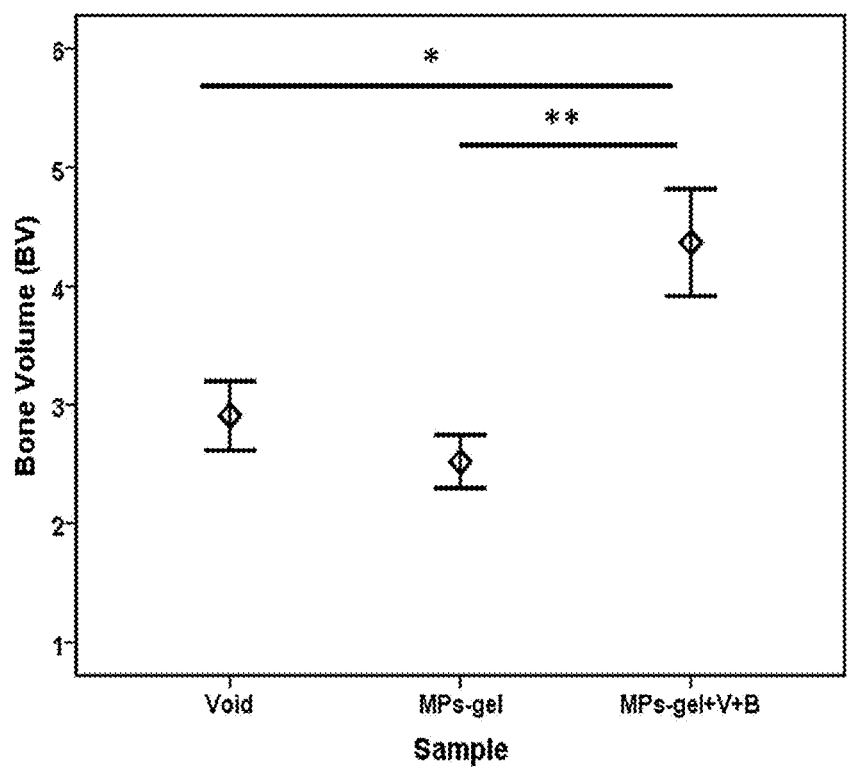
Figure 7C:
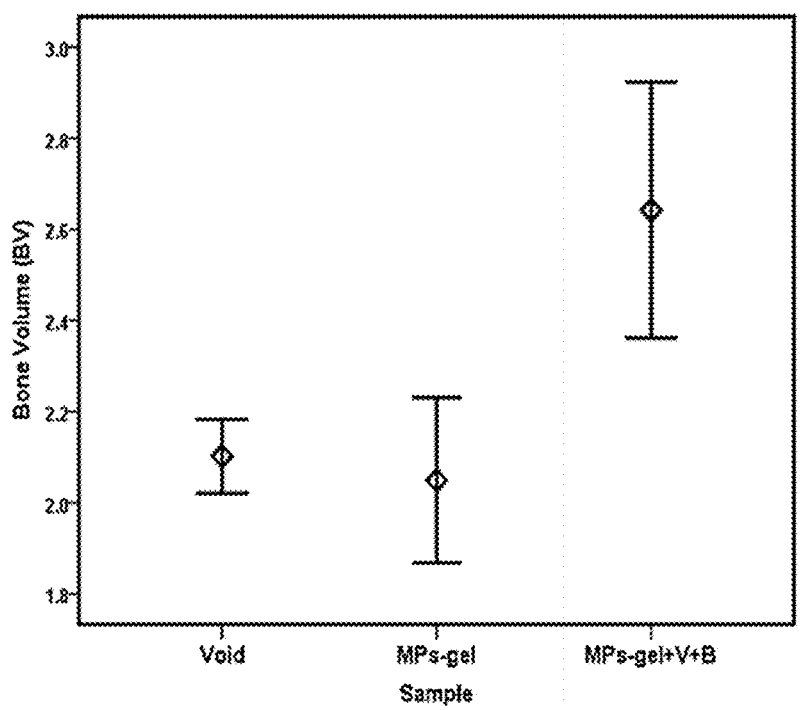

The positive results from the ectopic bone formation model indicated the use of an orthotopic bone formation model. FIG. 11 shows an illustration depicting the orthotopic surgical procedure. MPs-gel+V+B group with MSCs were omitted from this evaluation as the subcutaneous bone formation results showed no particular difference in bone formation with this group compared to without MSCs. The cranial defects were created on rats and the gel samples were injected, and the bone regeneration was studied using microCT for 12 weeks. MicroCT analysis and 3D rendering were performed for some samples at 6 weeks to observe the defect site and bone ingrowth. As observed in FIG. 7A, after 6 weeks, the bone fragments were growing towards the defect on all groups. The bone ingrowth, however, looked more prominent for the MPs-gel+V+B group with significant bone growing in the defect region. The results at 12 weeks further verified this observation with superior bone formation observed on this group with new bone covering whole defect region. The quantitative analysis of new bone formation measured as bone volume (BV) further showed a significantly high value of BV on MPs-gel+V+B group compared to MPs-gel ($p<0.001$) and void ($p<0.05$) groups. These results (FIG. 7B) show that the combination of VEGF with BMP-9 when delivered using MPs-gel induced the higher bone regeneration in the defects at a much lower dose of BMP-9 than conventionally used.

Figure 8A:
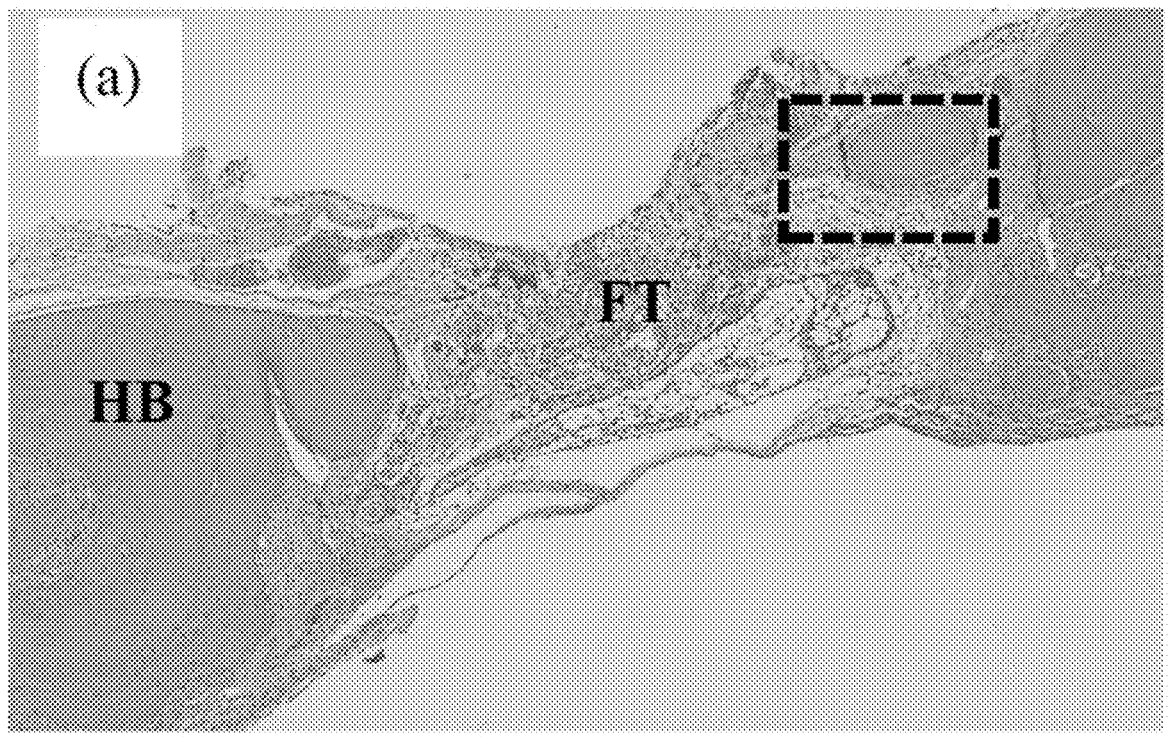
FIGS. 8A-8F: Histological sections of defect region harvested at 12 weeks and stained with H&E.
Figure 8B:
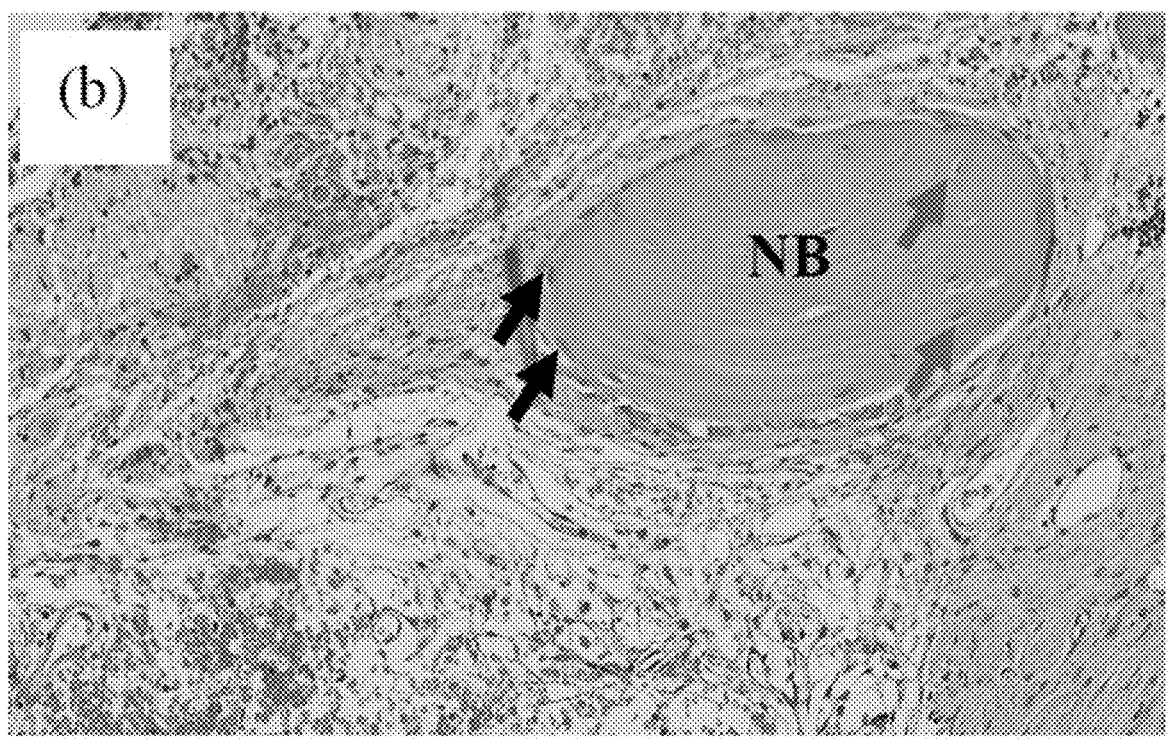
Figure 8C:
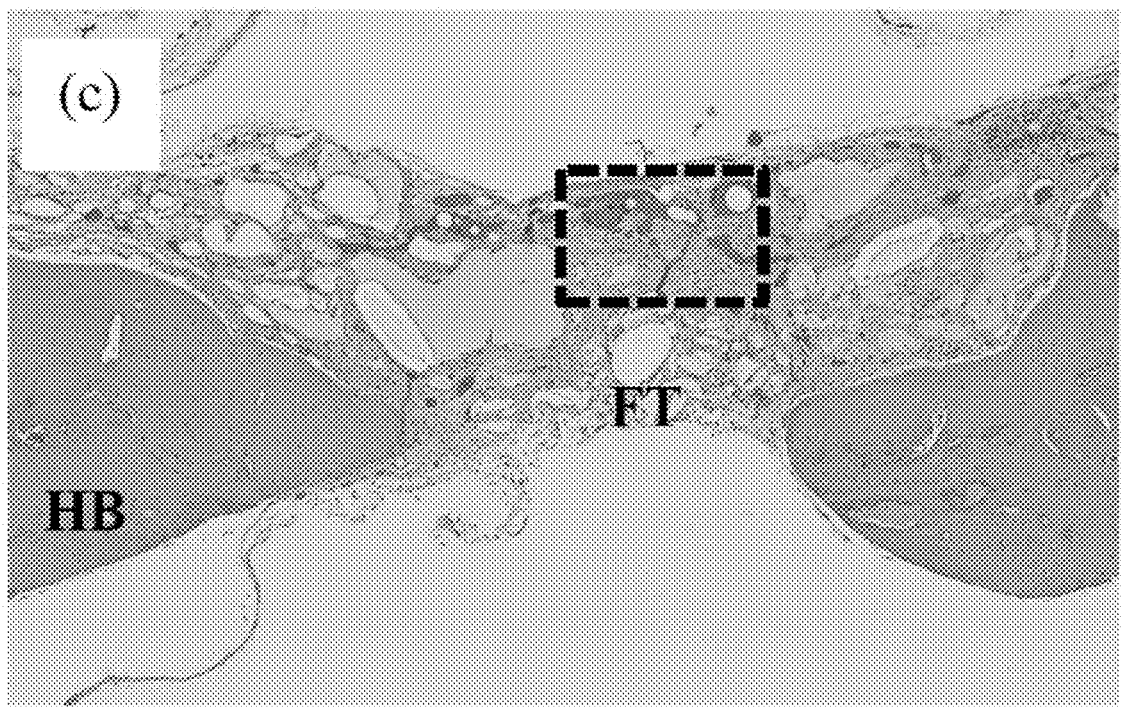
Figure 8D:
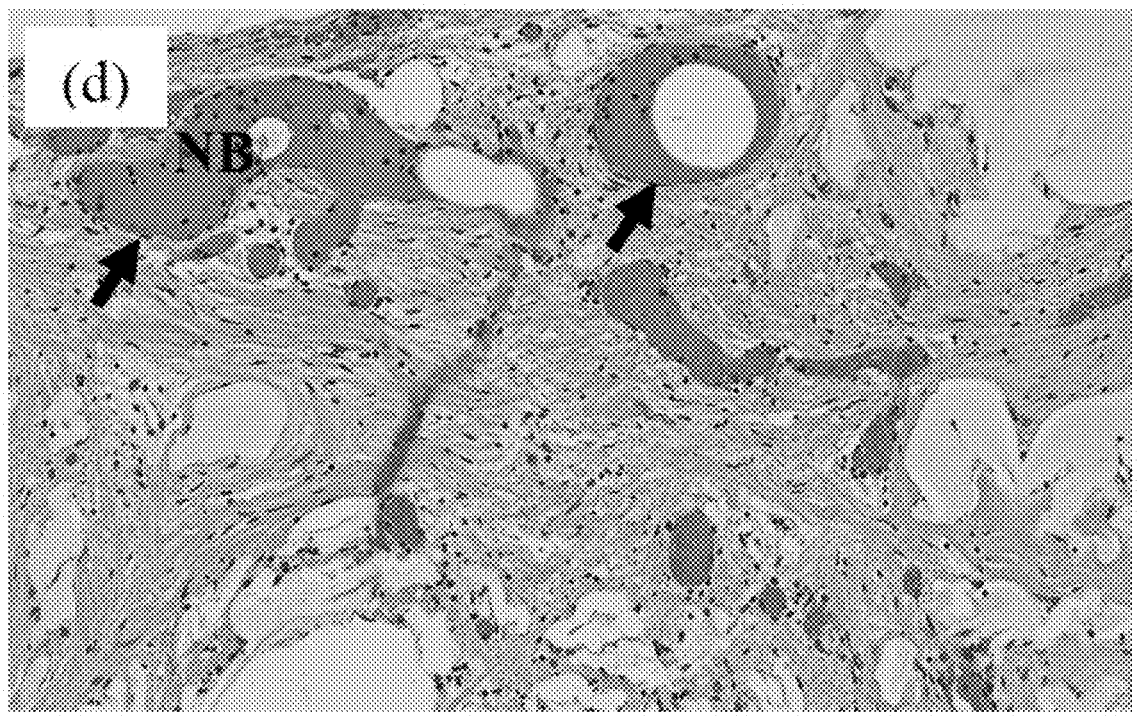
Figure 8E:
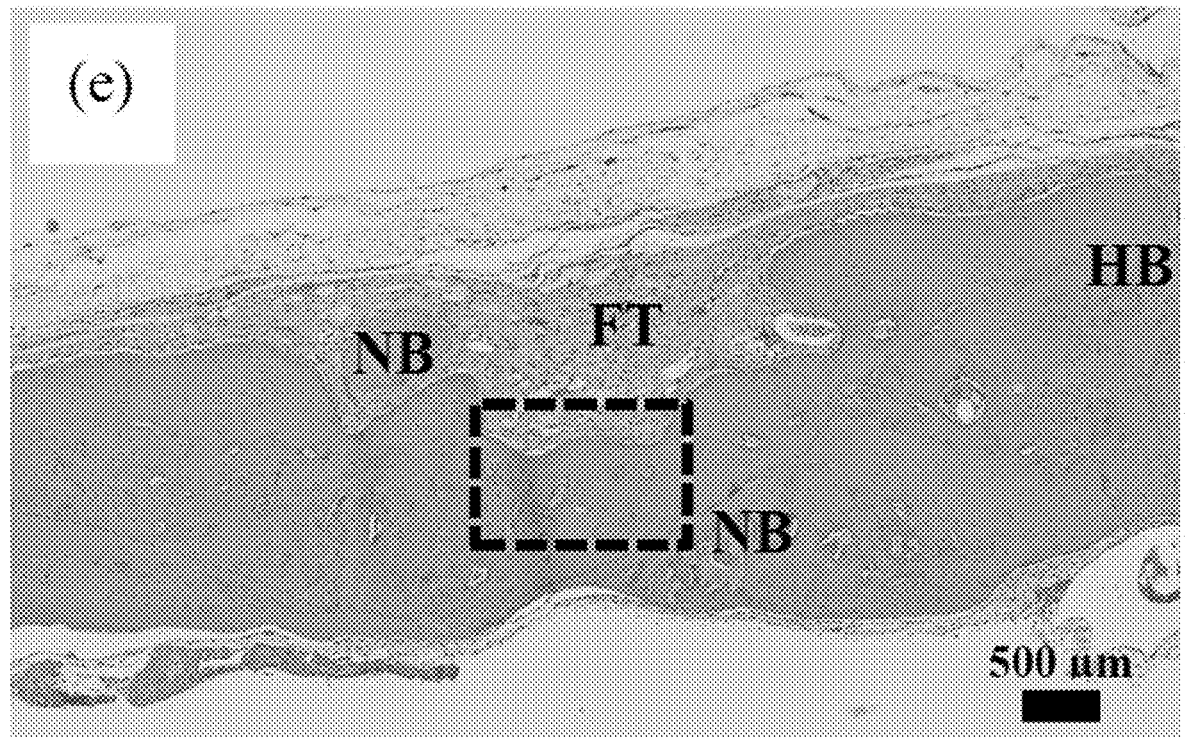
Figure 8F:
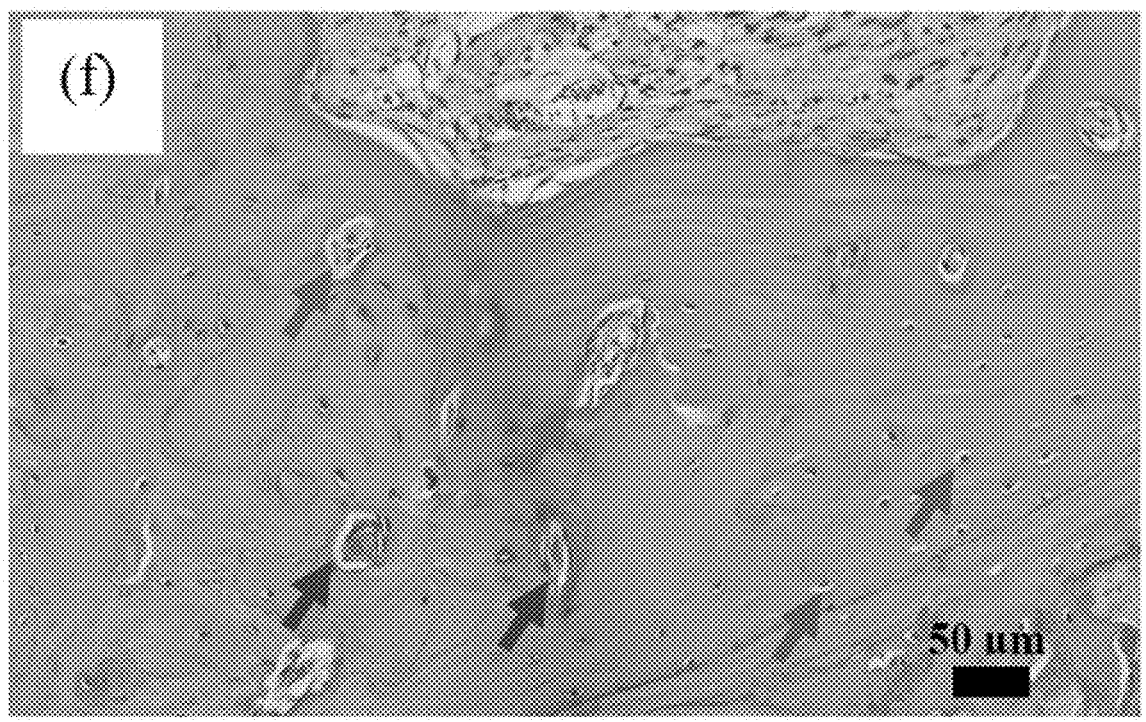

The bone regeneration was further studied using H&E staining at 12 weeks. Histological analysis revealed the nature of bone formation along the defect region. As shown in FIG. 8A, most of the new bone formation on the void defect was along the defect margin with few bone fragments on the central defect region but a majority of it filled with fibrous connective tissue. The MPs-gel group also showed similarly less bone formation with most of the defect region filled with fibrous connective tissues (FIG. 8C). The new bone formation on both of these groups looked immature, lacking osteoid and blood vessels as shown in magnified images in FIGS. 8B, 8D. In the case of MPs-gel+V+B, a complete bone formation was observed with new bone bridging the gap between the defects (FIG. 8E). The newly formed bone showed the abundant presence of osteoid and blood vessels (FIG. 8F). In sum, the histological analysis of new bone formation showed that the new bone formed was a matured bone with abundantly present blood vessels.

CONCLUSIONS

These examples describe a multicomponent releasing MPs-gel scaffold capable of facilitating BMP-9 induced bone formation at a low dose. The thermosensitive gel is an injectable medium for BMP-9 coated MPs such that their injectability property is preserved while also increasing the efficacy of BMP-9 at the injection site through the localization of MPs. BMP-9 coated on the MPs and VEGF introduced to the thermosensitive gel were both bioactive, and their temporal release profile enabled improved osteogenic responses. MPs-gel maintained the long term viability of encapsulated hMSCs. Furthermore, the MPs-gel with BMP-9 and VEGF were found to enhance both subcutaneous and cranial bone formation, indicated by significantly higher bone formation induced by MPs-gel+V+B group. Taken together, the results show that BMP-9 combined with VEGF when delivered through injectable microparticles-gel composites enhance the bone formation at a low dose of BMP-9. The samples were shown to induce both ectopic and cranial bone formation at the low dose of BMP-9 of 1 µg/ml.

Certain embodiments of the compositions and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A composition comprising:
    polymer microparticles coated with a first active substance, wherein the polymer microparticles comprise chitosan crosslinked with sodium tripolyphosphate;
    a thermoresponsive hydrogel comprising a crosslinker and a polymer blend of methylcellulose and alginate, wherein the crosslinker comprises calcium; and
    a second active substance incorporated into the thermoresponsive hydrogel;
    wherein the first active substance is a bone morphogenic protein and the second active substance is a growth factor.

2. The composition of claim 1, wherein the first active substance is present at a dose of from about 500 ng/ml to about 1 µg/ml.

3. The composition of claim 1, wherein the first active substance comprises BMP-2, BMP-7, BMP-9, or a combination thereof.

4. The composition of claim 1, wherein the second active substance is present at a dose of from about 500 ng/ml to about 1 µg/ml.

5. The composition of claim 1, wherein the first active substance consists essentially of BMP-9, and the second active substance consists essentially of VEGF.

6. The composition of claim 1, wherein the first active substance is capable of controlled release over a period of several weeks in vivo.

7. The composition of claim 1, wherein the second active substance is capable of controlled release over a period of several weeks in vivo.

8. The composition of claim 1, wherein each of the first active substance and the second active substance is capable of controlled release over a period of several weeks in vivo.

9. The composition of claim 1, wherein the polymer microparticles have a size ranging from about 300 µm to about 1 mm.

10. The composition of claim 1, wherein the composition gels at 37° C.

11. The composition of claim 1, wherein the composition is a liquid at 0° C.

12. The composition of claim 5, wherein the BMP-9 is present at a dose of from about 500 ng/ml to about 1 µg/ml.

13. A method for making a bone repair composition, the method comprising:
    coating polymer microparticles with a first active substance comprising a bone morphogenic protein to form coated microparticles, wherein the polymer microparticles comprise chitosan crosslinked with sodium tripolyphosphate; and adding the coated microparticles to a thermoresponsive hydrogel comprising a crosslinker and a polymer blend of methylcellulose and alginate to make a bone repair composition, wherein the crosslinker comprises calcium;

wherein a second active substance comprising a growth factor is incorporated into the thermoresponsive hydrogel.

14. The method of claim 13, wherein the bone repair composition is capable of gelling at 37° C.

15. The method of claim 13, wherein the polymer microparticles are rinsed, stirred, and dried to produce polymer microparticles having a size suitable for injection using a 13 G or 16 G needle.

* * * * *